United States Patent
Fiorini et al.

(10) Patent No.: US 12,005,102 B2
(45) Date of Patent: *Jun. 11, 2024

(54) ANTI-ABETA THERAPEUTIC VACCINES

(71) Applicant: AC Immune SA, Lausanne (CH)

(72) Inventors: Emma Fiorini, Lausanne (CH); Marija Vukicevic Verhille, Lausanne (CH); Maria Pihlgren Bosch, Lausanne (CH)

(73) Assignee: AC Immune SA, Lausanne (CH)

( * ) Notice: Subject to any disclaimer, the term of this patent is extended or adjusted under 35 U.S.C. 154(b) by 520 days.

This patent is subject to a terminal disclaimer.

(21) Appl. No.: 17/091,553

(22) Filed: Nov. 6, 2020

(65) Prior Publication Data

US 2021/0093700 A1  Apr. 1, 2021

Related U.S. Application Data

(63) Continuation of application No. 16/379,322, filed on Apr. 9, 2019, now Pat. No. 10,828,351.

(30) Foreign Application Priority Data

Apr. 10, 2018 (EP) .................................. 18166659
Oct. 24, 2018 (EP) .................................. 18202366

(51) Int. Cl.
| | |
|---|---|
| *A61K 39/395* | (2006.01) |
| *A61K 9/127* | (2006.01) |
| *A61K 39/00* | (2006.01) |
| *A61K 39/05* | (2006.01) |
| *A61K 39/08* | (2006.01) |
| *A61K 39/245* | (2006.01) |
| *A61K 39/39* | (2006.01) |
| *A61P 25/28* | (2006.01) |
| *C07K 14/005* | (2006.01) |

(52) U.S. Cl.
CPC .......... *A61K 39/0007* (2013.01); *A61K 9/127* (2013.01); *A61K 39/0003* (2013.01); *A61K 39/0005* (2013.01); *A61K 39/05* (2013.01); *A61K 39/08* (2013.01); *A61K 39/245* (2013.01); *A61K 39/39* (2013.01); *A61P 25/28* (2018.01); *C07K 14/005* (2013.01); *A61K 2039/55516* (2013.01); *A61K 2039/55555* (2013.01); *A61K 2039/55572* (2013.01); *A61K 2039/57* (2013.01); *A61K 2039/575* (2013.01); *A61K 2039/58* (2013.01); *A61K 2039/627* (2013.01); *A61K 2039/645* (2013.01); *A61K 2039/70* (2013.01); *C07K 2319/33* (2013.01); *C07K 2319/55* (2013.01); *C12N 2710/16232* (2013.01); *C12N 2710/16234* (2013.01); *C12N 2760/16033* (2013.01)

(58) Field of Classification Search
None
See application file for complete search history.

(56) References Cited

U.S. PATENT DOCUMENTS

| | | | | |
|---|---|---|---|---|
| 7,807,175 | B2 * | 10/2010 | Pfeifer | A61P 3/10 |
| | | | | 424/812 |
| 10,828,351 | B2 * | 11/2020 | Fiorini | A61K 39/0005 |
| 2011/0070298 | A1 | 3/2011 | Mansour | |
| 2014/0271690 | A1 | 9/2014 | Wang | |

FOREIGN PATENT DOCUMENTS

| | | |
|---|---|---|
| CN | 105418767 A | 3/2016 |
| EP | 1992639 | 11/2008 |
| WO | WO 2001062284 | 8/2001 |
| WO | 2002066056 | 8/2002 |
| WO | 2003015812 | 2/2003 |
| WO | 2004006861 | 1/2004 |
| WO | WO 2006133196 | 12/2006 |
| WO | WO 2007068411 | 6/2007 |
| WO | 2009029272 | 3/2009 |
| WO | WO 2009090650 | 7/2009 |
| WO | WO 2010016912 | 2/2010 |
| WO | WO 2011031298 | 3/2011 |
| WO | WO 2011115483 | 9/2011 |

(Continued)

OTHER PUBLICATIONS

Agadjanyan et al. (2005) "Prototype Alzheimer's Disease Vaccine Using the Immunodominant B Cell Epitope from β-Amyloid and Promiscuous T Cell Epitope Pan HLA DR-Binding Peptide" J Immunol., 174(3):1580-1586.
Arai et al. (2015) "Vanutide cridificar and the QS-21 adjuvant in Japanese subjects with mild to moderate Alzheimer's disease: results from two phase 2 studies" Curr Alzheimer Res., 12(3):242-254.
Boeckler et al. (1999) "Design of Highly Immunogenic Liposomal Constructs Combining Structurally Independent B Cell and T Helper Cell Peptide Epitopes" Euro. J. of Immun., 29(7):2297-2308.

(Continued)

*Primary Examiner* — Yunsoo Kim
(74) *Attorney, Agent, or Firm* — Brian E. Davy; Bozicevic, Field & Francis LLP

(57) ABSTRACT

A liposomal vaccine composition comprises a β-amyloid (Aβ)-derived peptide antigen displayed on the surface of the liposome. The vaccine composition also comprises a peptide comprising a universal T-cell epitope encapsulated within the liposome. The vaccine composition also comprises an adjuvant, which may form part of the liposome and may be displayed at least in part on the surface of the liposome. These vaccine compositions are used for treating, preventing, inducing a protective immune response against or alleviating the symptoms associated with an amyloid-beta associated disease or condition or a condition characterised by, or associated with, loss of cognitive memory capacity in a subject. The vaccine compositions may be provided as a kit. Related methods of producing a liposomal vaccine composition are also provided.

23 Claims, 6 Drawing Sheets

Specification includes a Sequence Listing.

(56) References Cited

FOREIGN PATENT DOCUMENTS

| WO | WO 2012020124 | 2/2012 |
|---|---|---|
| WO | WO 2012055933 | 5/2012 |
| WO | WO2016062720 | 4/2016 |
| WO | WO 2013049941 | 4/2023 |

OTHER PUBLICATIONS

Diethelm-Okita et al. (2000) "Universal epitopes for human CD4+ cells on tetanus and diphtheria toxins" J. of Infectious Diseases, 181(3):1001-1009.

Fraser et al. (2014) "Generation of a universal CD4 memory T cell recall peptide effectivein humans, mice and non-human primates" Vaccine, 32:2896-2903.

Ghochikyan et al. (2006) "Prototype Alzheimer's disease epitope vaccine induced strong Th2-type anti-Abeta antibody response with Alum to Quil A adjuvant switch" Vaccine, 20;24(13):2275-2282.

Ghochikyan et al. (2013) "Refinement of a DNA based Alzheimer disease epitope vaccine in rabbits" Human Vaccines and Immunotherapeutics, 9(5): 1002-1010.

Gilman et al. (2005) "Clinical effect of Aβ immunization (AN1792) in patients with AD in an interrupted trial" Neurology, 64:1553-1562.

Hickman et al. (2011) "Sequence-independent Control of Peptide Conformation in Liposomal Vaccines for Targeting Protein Misfolding Diseases" J. Biol. Chem., 286(16):13966-13976.

Hills et al. (2016) "A Rapid-Response Humoral Vaccine Platform Exploiting Pre-Existing Non-Cognate Populations of Anti-Vaccine or Anti-Viral CD4+ T Helper Cells to Confirm B Cell Activation" PLoS ONE, 11(11):e0166383. doi:10.1371/journal.pone.0166383.

International Search Report and Written Opinion dated Jul. 24, 2019, Appl. No. PCT/EP2019/058980, 16 pp.

Liu et al. (2013) "MER5101, a novel Aβ1-15:DT conjugate vaccine, generates a robust anti-Aβ antibody response and attenuates Aβ pathology and cognitive deficits in APPswe/PS1ΔE9 transgenic mice" J Neurosci., 33(16):7027-7037.

Lutzner (2008) "Quantifying Cathepsin S Activity in Antigen Presenting Cells Using a Novel Specific Substrate" J. Biol. Chem., 283(52):36185.

Maier et al. (2006) "Short amyloid-β (Aβ) immunogens reduce cerebral Aβ load and learning deficits in an Alzheimer's disease mouse model in the absence of an Aβ-specific cellular immune response" J Neurosci., 3;26(18):4717-4728.

Monsonego and Weiner (2003) "Immunotherapeutic approaches to Alzheimer's disease" Science, 31;302(5646):834-838.

Muhs et al. (2007) "Liposomal vaccines with conformation-specific amyloid peptide antigens define immune response and efficacy in APP transgenic mice" PNAS, 104(23):9810-9815.

Orgogozo et al. (2003) "Subacute meningoencephalitis in a subset of patients with AD after Aβ42 immunization" Neurology, 61:46-54.

Pihlgren et al. (2013) "TLR4 and TRIF-dependent stimulation of B lymphocytes by peptide liposomes enables T-cell independent isotype switch in mice" Blood, 121(1):85-94.

Schneeberger et al. (2010) "AFFITOME® technology in neurodegenerative diseases: the doubling advantage" Hum Vaccin., 11:948-952.

Seabrook et al. (2006) "Dendrimeric Aβ1-15 is an effective immunogen in wildtype and APP-tg mice" Neurobiol Aging, 28(6):813-823.

Winblad et al. (2012) "Safety, tolerability, and antibody response of active Aβ immunotherapy with CAD106 in patients with Alzheimer's disease: randomised, double-blind, placebo-controlled, first-in-human study" Lancet Neurol., 11(7):597-604.

Rosset et al., (2015) "Vaccine-induced Aβ-specific $CD8^+T$ cells do not trigger autoimmune neuroinflammation in a murine model of Alzheimer's disease." Journal of Neuroinflammation, vol. 12, No. 95, 14 pages.

Substantive Report dated Dec. 9, 2022, Colombian application No. NC2020/0013977, English translation, 10 pages.

Examination Report dated May 4, 2023, Appl. No. EP 19716161.5, 7 pp.

Nicolau et al. (2002) "A liposome-based therapeutic vaccine against β-amyloid plaques on the pancreas of transgenic NORBA mice" PNAS, 99(4):2332-2337.

Office Action dated Jun. 6, 2023, Appl. No. JP 2020-555339, 6 pp.

Tahira (2016) "Immunotherapy targeting Aβ for Alzheimer's disease" Neurotherapy, 33(3):415-419. (English abstract only).

Hanson et al. (2015) "Liposomal vaccines incorporating molecular adjuvants and infrastructural T-cell help promote the immunogenicity of HIV membrane-proximal external region peptides." Vaccine, vol. 33, pp. 861-868.

Office Action dated Aug. 22, 2023, Appl. No. JP 201980034976.1, 8 pp.

\* cited by examiner

SEQUENCE LISTING

<160> NUMBER OF SEQ ID NOS: 12

<210> SEQ ID NO 1
<211> LENGTH: 40
<212> TYPE: PRT
<213> ORGANISM: Artificial sequence
<220> FEATURE:
<223> OTHER INFORMATION: Synthetic peptide

<400> SEQUENCE: 1

Val His His Asn Thr Glu Glu Ile Val Ala Gln Ser Ile Ala Leu Ser
1               5                   10                  15

Ser Leu Met Val Pro Met Gly Ala Pro Gln Tyr Ile Lys Ala Asn Ser
            20                  25                  30

Lys Phe Ile Gly Ile Thr Glu Leu
        35                  40

<210> SEQ ID NO 2
<211> LENGTH: 57
<212> TYPE: PRT
<213> ORGANISM: Artificial sequence
<220> FEATURE:
<223> OTHER INFORMATION: Synthetic peptide

<400> SEQUENCE: 2

Val Tyr Gly Gly Ser Lys Thr Ser Leu Tyr Asn Leu Arg Arg Gly Thr
1               5                   10                  15

Ala Leu Ala Ile Val Val Arg Gln Tyr Ile Lys Ala Asn Ser Lys Phe
            20                  25                  30

Ile Gly Ile Thr Glu Leu Val Val Arg Pro Ile Phe Phe Leu His His
        35                  40                  45

Ser Asn Thr Asp Arg Leu Trp Ala Ile
    50                  55

<210> SEQ ID NO 3
<211> LENGTH: 38
<212> TYPE: PRT
<213> ORGANISM: Artificial sequence
<220> FEATURE:
<223> OTHER INFORMATION: Synthetic peptide

<400> SEQUENCE: 3

Val Tyr Gly Gly Ser Lys Thr Ser Leu Tyr Asn Leu Arg Arg Gly Thr
1               5                   10                  15

Ala Leu Ala Ile Val Val Arg Gln Tyr Ile Lys Ala Asn Ser Lys Phe
            20                  25                  30

Ile Gly Ile Thr Glu Leu
        35

<210> SEQ ID NO 4
<211> LENGTH: 52
<212> TYPE: PRT
<213> ORGANISM: Artificial sequence
<220> FEATURE:
<223> OTHER INFORMATION: Synthetic peptide

<400> SEQUENCE: 4

Ser Met Gly Val Tyr Gln Ile Leu Ala Ile Tyr Ser Thr Val Val Arg
1               5                   10                  15

Ile Val Ala Gln Ser Ile Ala Leu Ser Ser Val Val Arg Tyr Ile Lys
            20                  25                  30

Ala Asn Ser Lys Phe Ile Gly Val Val Arg Leu Tyr Asn Leu Arg Arg

```
<210> SEQ ID NO 5
<211> LENGTH: 50
<212> TYPE: PRT
<213> ORGANISM: Megathura crenulata

<400> SEQUENCE: 5

Ser Thr Leu Glu Tyr Phe Leu Tyr Asp Pro Ile Phe Phe Leu His His
1               5                   10                  15

Ser Asn Thr Asp Arg Leu Trp Ala Ile Trp Gln Ala Leu Gln Lys Tyr
            20                  25                  30

Arg Gly Lys Pro Tyr Asn Thr Ala Asn Cys Ala Ile Val Arg His Asp
        35                  40                  45

Thr Tyr
    50

<210> SEQ ID NO 6
<211> LENGTH: 20
<212> TYPE: PRT
<213> ORGANISM: Corynebacterium diphtheriae

<400> SEQUENCE: 6

Val His His Asn Thr Glu Glu Ile Val Ala Gln Ser Ile Ala Leu Ser
1               5                   10                  15

Ser Leu Met Val
            20

<210> SEQ ID NO 7
<211> LENGTH: 25
<212> TYPE: PRT
<213> ORGANISM: Influenza virus

<400> SEQUENCE: 7

Ile Asp Gly Val Lys Leu Glu Ser Met Gly Val Tyr Gln Ile Leu Ala
1               5                   10                  15

Ile Tyr Ser Thr Val Ala Ser Ser Leu
            20                  25

<210> SEQ ID NO 8
<211> LENGTH: 20
<212> TYPE: PRT
<213> ORGANISM: Human herpesvirus 4

<400> SEQUENCE: 8

Val Tyr Gly Gly Ser Lys Thr Ser Leu Tyr Asn Leu Arg Arg Gly Thr
1               5                   10                  15

Ala Leu Ala Ile
            20

<210> SEQ ID NO 9
<211> LENGTH: 5
<212> TYPE: PRT
<213> ORGANISM: Artificial sequence
<220> FEATURE:
<223> OTHER INFORMATION: Synthetic peptide

<400> SEQUENCE: 9

Thr Val Gly Leu Arg
1               5
```

```
<210> SEQ ID NO 10
<211> LENGTH: 5
<212> TYPE: PRT
<213> ORGANISM: Artificial sequence
<220> FEATURE:
<223> OTHER INFORMATION: Synthetic peptide

<400> SEQUENCE: 10

Lys Val Ser Val Arg
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic peptide

<400> SEQUENCE: 11

Pro Met Gly Ala Pro
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic peptide

<400> SEQUENCE: 12

Pro Met Gly Leu Pro
1               5
```

ANTI-ABETA THERAPEUTIC VACCINES

CROSS-REFERENCE TO RELATED APPLICATIONS

This application is a continuation of U.S. patent application Ser. No. 16/379,322 filed on Apr. 9, 2019, which claims the benefit of European Patent Application No. 18166659.5, filed Apr. 10, 2018, and European Patent Application No. 18202366.3, filed Oct. 24, 2018, which applications are incorporated herein by reference in their entireties.

FIELD OF THE INVENTION

The invention relates to anti-abeta therapeutic vaccines and their use in treatment and prevention of disease. The vaccines incorporate Aβ-derived peptide B-cell antigens and T cell epitopes.

DESCRIPTION

Alzheimer's Disease (AD) is a devastating, progressive degenerative disorder characterized by loss of cognitive functions, including memory, as well as the loss of ability to perform regular daily activities. AD affects approximately 40 million patients worldwide, with the number increasing rapidly as the population ages. The major neuropathological change in the brain of AD patients is neuronal death, mainly in memory and cognition-related regions (Soto, 1999). One of the most striking pathological features of AD is the abundant presence of amyloid beta (Aβ) plaques in brains of diseased individuals (Soto, 1999). Aβ plaques are formed by the 39 to 43 amino acid long Aβ peptide, which is in random coil conformation in its natural non-pathological form. During the transition to the pathological state, it transforms mainly into a β-sheet secondary structure, spontaneously aggregating into insoluble deposits.

The few currently available treatments for AD are considered to be primarily symptomatic in their action. Despite significant efforts put into developing treatments over the years, no disease modifying treatment for AD has been approved up to date. Attempts have been made in order to develop an immunotherapeutic that would neutralize pathological Aβ in the diseased brain over the long term (Winblad, 2014). Vaccines present the advantage of stimulating the immune system to produce a pool of slightly different, but very specific antibodies, while the response can be further recalled by additional vaccinations, if needed. However, an active immunization (vaccination) approach against Aβ represents several main challenges. Amyloid beta is a so-called self-antigen, which the human body is constantly exposed to. Therefore, it is quite difficult to break immune tolerance and induce an antibody response against it. In addition, it is quite difficult to induce a strong immune response to a vaccine in elderly and sick people, such as AD patients, due to their weakened immune system and decreased number of immune cells.

Despite these challenges, in an initial study, a full-length Aβ1-42 vaccine (AN1792) induced an antibody response and a promising efficacy, with a slower rate of cognitive decline in patients who had received vaccination than in placebo-treated patients (Gilman, 2005). However, 6% of treated patients developed meningoencephalitis, an inflammatory reaction considered to be due to a T-cell-mediated response against full length Aβ1-42 (Orgogozo, 2003).

Another known anti-Aβ vaccine, ACI-24, contains a sequence of 15-amino acids with complete identity with the human sequence 1-15 of Aβ (WO2007/068411). This peptide antigen is linked to a liposomal carrier with the aim to stimulate antibodies against Aβ, while avoiding meningoencephalitis and hemorrhage (Muhs, 2007, Pihlgren, 2013). The choice of the Aβ1-15 peptide serving as the antigen was based on the rationale that this sequence contains a B-cell epitope, but lacks a strong T-cell reactive site of full-length Aβ1-42 (Monsonego, 2003), the latter being considered to be the cause of the unwanted inflammatory reactions. ACI-24 has been shown to act through a simultaneous activation of a B-cell receptor specific for Aβ1-15 and the Toll-like receptor 4 (TLR4), activated by monophosphoryl lipid A (MPLA), adjuvant present in the ACI-24 vaccine (Pihlgren, 2013). B-cells are activated to proliferate and produce immunoglobulin (Ig) by cross-linking the B-cell surface Ig receptor. In order to increase antibody production, a second signal can be provided by a T helper cell activated by a T-cell epitope. T-cell epitopes, presented by the major histocompatibility complex (MHC) molecules (in human called human leucocyte antigen (HLA)) on the surface of an antigen-presenting cell (APC), promote the differentiation of cognate T helper cells capable of producing IFNγ and IL-4. Cytokine release and co-stimulatory signals between activated T and B cells increase antibody responses and class-switching. After primary vaccination, naïve T cells proliferate and differentiate into effector cells. A small fraction of these cells will form the pool of long-lived memory T cells, capable of quickly proliferating upon re-encountering the cognate peptide after vaccine boosting (Sallusto, 2010). So-called "universal" T-cell epitopes are specific to the T-cells that are present in the vast majority of the human population. They commonly originate from antigens to which humans are normally exposed during their lifetime (e.g. tetanus, influenza, etc.). The ability of a T-cell epitope to activate T cells is the result of at least two complementary properties: i) affinity of binding to the HLA groove, meaning the strength of the binding, as well as ii) its capacity to bind different HLA haplotypes in a promiscuous manner, meaning the ability to cover very diverse human populations, with regards to the differences in the expression of HLA molecules.

There exists a need for developing an anti-Aβ vaccine that is highly immunogenic while maintaining a good safety profile. This need has been met by incorporating a universal T-cell epitope inside the liposomal ACI-24 vaccine. Since the ACI-24 vaccine displays Aβ1-15 on the surface of the liposome, inclusion of universal T-cell epitopes on the surface of the liposome was considered by the inventors as the first choice route to improving efficacy of the vaccine. Surprisingly, however, inclusion of universal T-cell epitopes on the surface of the liposome was not able to increase (or substantially increase) the efficacy of the vaccine. Thus, as explained herein, an encapsulation approach was adopted which was shown to provide improved efficacy. The incorporation of a universal T-cell epitope inside the liposomal vaccine has been shown herein to increase (or substantially increase) the efficacy of the vaccine while maintaining a good safety profile through a T-cell activation that is not directed toward Aβ. There were, however, several challenges with developing such an approach. Firstly, the universal T-cell epitopes developed herein tend to be hydrophobic which makes encapsulation in the liposome difficult. Secondly, in order to improve immunogenicity, multiple universal T-cell epitopes were often combined. However, the peptide synthesis yield and success rate is lowered as the length of the peptides increases. Thirdly, the charge of the selected universal T-cell epitopes influences the efficiency of encapsulation and the experimental conditions required to ensure encapsulation; due to the negatively charged liposomal membrane.

Accordingly, the invention provides a liposomal vaccine composition comprising:
  a. A β-amyloid (Aβ)-derived peptide B-cell antigen displayed on the surface of the liposome; and
  b. A peptide comprising a universal T-cell epitope encapsulated within the liposome.

A particularly preferred vaccine composition comprises the ACI-24 vaccine modified so as to include a peptide comprising a universal T-cell epitope encapsulated within the liposome. A liposome is an example of a carrier. Thus, the carrier is generally a liposome but may be any carrier that is suitable to present the Aβ-derived peptide antigen on the surface in the same manner as achieved by a liposome (in which the Aβ-derived peptide antigen adopts a predominantly β-sheet conformation) and also encapsulate a peptide comprising a universal T-cell epitope. Examples include vesicles and particulate bodies.

By "universal T-cell epitope" is meant an epitope that is specific to T-cells that are present in the majority of the human population. They commonly originate from antigens to which humans are normally exposed during their lifetime. Examples include antigens incorporated in routinely administered vaccines. Specific examples are T-cell epitopes included in tetanus, influenza and diphtheria, and also Keyhole limpet hemocyanin (KLH) and Epstein Barr virus (EBV). The "universal" ability of a T-cell epitope to activate T cells is the result of at least two complementary properties: i) affinity of binding to the HLA groove, meaning the strength of the binding, as well as ii) its capacity to bind different HLA haplotypes in a promiscuous manner, meaning the ability to cover very diverse human populations, with regards to the differences in the expression of HLA molecules. The universal T-cell epitopes may bind to a majority of MHC class II alleles present in the human population. The universal T-cell epitopes included in the vaccine compositions of the invention may thus be capable of stimulating a CD4 T-cell response. The universal T-cell epitopes included in the vaccine compositions of the invention may thus be capable of stimulating a helper T-cell response that enhances (Aβ-specific) antibody production by B-cells.

The universal T-cell epitopes included in the vaccine compositions of the invention are typically synthesized by solid phase synthesis. Thus, in some embodiments, the universal T-cell epitopes are synthesized by solid phase synthesis. This and other practical challenges of encapsulation mean that, in some non-limiting embodiments, the peptide comprising a universal T-cell epitope is no more than 85, 80, 75 or 70 amino acids in length. The minimum length of a T-cell epitope peptide to ensure a sufficient immunogenicity is typically around 10 amino acids. Thus, the minimum length of the peptide is typically around 10 amino acids to ensure a sufficiently immunogenic T-cell epitope is generated. In some embodiments, the peptide is at least 20 amino acids in length. In other embodiments the peptide is between 30 and 60 amino acids in length; this is based on the preferred minimum length per universal T-cell epitope and the preference for a peptide comprising at least two, three or four (linked) universal T cell epitopes.

It has also been found that universal T-cell epitopes of utility according to the present invention are typically hydrophobic. This provides further challenges for their synthesis, purification and encapsulation within liposomes, due to their interactions with the lipids. Percentage hydrophobicity is calculated by dividing the total number of hydrophobic amino acids (Phe, Ile, Leu, Met, Val, Trp, Ala and Pro) by the total number of amino acids in either the overall peptide comprising the universal T-cell epitope (when considering the overall peptide) or in the individual T-cell epitope (when considering each universal T-cell epitope individually) and multiplying by 100. Hydrophobic amino acids for the present purposes are defined as leucine (Leu), isoleucine (Ile), phenylalanine (Phe), tryptophan (Trp), valine (Val), methionine (Met), proline (Pro) and alanine (Ala).

Thus, generally, the peptide comprising a universal T-cell epitope comprises at least 30% hydrophobic amino acids. This means that at least 30% of the amino acids in the overall peptide comprising the universal T-cell epitope are hydrophobic amino acids. The majority of the tested peptides comprising universal T-cell epitopes contain up to 50% hydrophobic amino acids. In some instances, the peptide may comprise at least 35%, 40%, 45%, or 50% hydrophobic amino acids.

In order to improve levels of immunogenicity, it is preferred that the vaccine composition comprises at least two different universal T-cell epitopes encapsulated within the liposome. Due to liposomal capacity, in combination with the hydrophobicity of the peptides and synthesis constraints, ideally each universal T-cell epitope is typically no more than 30 amino acids in length, preferably no more than 20 amino acids in length and still more preferably in the region of around 10-20 amino acids in length. As explained further herein, the inventors have found that longer universal T-cell epitopes can be effectively trimmed to a length of 10-20 amino acids whilst retaining immunogenicity. The trimmed peptides were designed by selecting, in the sequence of each individual T-cell epitope, the most immunogenic shorter subsequence, typically around 15 amino acids in length, based on in silico predicted T-cell epitope hotspots. Various software programs are available to assist with performance of this analysis, including the EpiVax immunogenicity screening platform (access via http://www.epivax.com). Further examples include the SYFPEITHI database (see Hans-Georg Rammensee, Jutta Bachmann, Niels Nikolaus Emmerich, Oskar Alexander Bachor, Stefan Stevanovic: SYFPEITHI: database for MHC ligands and peptide motifs. Immunogenetics (1999) 50: 213-219; access via www.syfpeithi.com), the SVMHC database (www.ncbi.nlm.nih.gov/pubmed/16844990) and the IEDB database (Vita R, Overton J A, Greenbaum J A, Ponomarenko J, Clark J D, Cantrell J R, Wheeler D K, Gabbard J L, Hix D, Sette A, Peters B. The immune epitope database (IEDB) 3.0. Nucleic Acids Res. 2014 Oct. 9. pii: gku938. [Epub ahead of print] PubMed PMID: 25300482; access via http://www.iedb.org/).

In some embodiments, each universal T-cell epitope comprises at least 30% hydrophobic amino acids. This means that at least 30% of the amino acids in the individual universal T-cell epitope are hydrophobic amino acids. For specific epitopes this figure may be as high as 80% hydrophobic amino acids. In some instances, there may be at least 40%, 45%, 50%, 55%, 60%, 65%, 70%, 75% or 80% hydrophobic amino acids. The maximum may be 80% hydrophobic amino acids in some embodiments, meaning the broadest range may be 30% to 80% hydrophobic amino acids.

In order to balance improved immunogenicity with the practical challenges of encapsulation, the vaccine composition may comprise two, three or four different universal T-cell epitopes encapsulated within the carrier. Where larger numbers of different universal T-cell epitopes are encapsulated (especially 3 or 4) it is preferred that they are trimmed to a length of around 10-20 amino acids, such as around 15 amino acids. It is preferred that multiple different universal T-cell epitopes are included in the same peptide that is encapsulated. Thus, synthetic peptide constructs containing multiple different universal T-cell epitopes represent a preferred implementation of the invention. In certain embodiments the peptide comprises at least two different universal T-cell epitopes. In more specific embodiments, the peptide comprises two, three or four universal T-cell epitopes. Where multiple (e.g. two, three or four) universal T-cell epitopes are included in a synthetic peptide construct, at least two of such epitopes may be joined by a linker. The linker is used to physically connect the universal T-cell epitopes to one another in a manner that does not detract from the immunogenicity of the linked epitopes. Suitable linkers for joining amino acids to one another are well known in the art. Preferred linkers are themselves amino acid based linkers, i.e. peptide linkers. They can thus join the universal T-cell epitopes to one another through peptide bonds. The linker is one which enables correct processing of the universal T-cell epitopes. Antigen presentation by MHC class II molecules requires the entry of antigens into the endosomal-lysosomal compartment. These antigens are then processed by proteolytic enzymes, of which the lysosomal cysteine proteases of the papain family constitute an important subset. The generated peptides bind to MHC class II molecules, which are then displayed at the surface of professional antigen presenting cells (APCs) including macrophages, dendritic cells (DCs) and B cells (Lutzner and Kalbacher 2008). Thus, preferably the linker comprises a substrate for a lysosomal cysteine protease of the papain family. The linker may comprise a substrate for one or more of cathepsin S, cathepsin B and cathepsin L. In some embodiments, the linker comprises, consists essentially of, or consists of at least two or at least three amino acids. In some embodiments, the linker comprises, consists essentially of, or consists of the amino acids VVR, TVGLR (SEQ ID NO:9), KVSVR (SEQ ID NO:10), PMGAP (SEQ ID NO:11) or PMGLP (SEQ ID NO:12).

The peptides comprising two universal T-cell epitopes may, therefore, be linear peptides in the format:
[universal T-cell epitope 1]-[linker]-[universal T-cell epitope 2]

The peptides comprising three universal T-cell epitopes may, therefore, be linear peptides in the format:
[universal T-cell epitope 1]-[linker]-[universal T-cell epitope 2]-[linker]-[universal T-cell epitope 3]

The peptides comprising four universal T-cell epitopes may, therefore, be linear peptides in the format:
[universal T-cell epitope 1]-[linker]-[universal T-cell epitope 2]-[linker]-[universal T-cell epitope 3]-[linker]-[universal T-cell epitope 4]

It should be noted that the linkers do not have to be identical between each pair of linked universal T-cell epitopes. Thus, for example, the linker between universal T-cell epitope 1 and universal T-cell epitope 2 could be different from the linker between universal T-cell epitope 2 and universal T-cell epitope 3. In the case of four universal T-cell epitopes each of the three linkers could be different or two could be the same and the third different (in any order). In some embodiments where multiple linkers are included in the peptide they are all identical.

The inventors have screened a range of sources of universal T-cell epitopes when devising suitable peptides for encapsulation. In some embodiments, the universal T-cell epitopes are derived from diphtheria toxin, tetanus toxin, Epstein Barr Virus, influenza hemagglutinin and/or keyhole limpet hemocyanin. Specific preferred combinations of universal T-cell epitopes are therefore selected from:
  a. A combination of a diphtheria toxin and tetanus toxin universal T-cell epitope
  b. A combination of an Epstein Barr Virus and tetanus toxin universal T-cell epitope
  c. A combination of an Epstein Barr Virus, tetanus toxin and keyhole limpet hemocyanin universal T-cell epitope; or
  d. A combination of an influenza hemagglutinin, diphtheria toxin, tetanus toxin and Epstein Barr Virus universal T-cell epitope Such combinations are preferably provided in the linker format explained above. For the avoidance of doubt, whilst the combinations are preferably included in the order specified, they may be included in an alternative order. For example, if there are three universal T-cell epitopes, A, B and C, they may be included in any of orders ABC, ACB, BAC, BCA, CAB or CBA.

Specific peptides comprising multiple different universal T-cell epitopes form a further aspect of the invention. Such peptides are preferably included in the vaccine compositions of the invention. Thus, peptides useful in the invention comprise, consist essentially of or consist of an amino acid sequence selected from SEQ ID NO: 1 (SAT42), SEQ ID NO: 2 (SAT43), SEQ ID NO: 3 (SAT44), SEQ ID NO: 4 (SAT47). The composition of these peptides is explained in more detail with reference to Table 2 below.

Specific peptides comprising a single universal T-cell epitope also form a further aspect of the invention. Such peptides are preferably included in the vaccine compositions of the invention. Thus, peptides useful in the invention comprise, consist essentially of or consist of an amino acid sequence selected from SEQ ID NO: 5 (SAT6), SEQ ID NO: 6 (SAT13), SEQ ID NO: 7 (SAT15), SEQ ID NO: 8 (SAT17). The composition of these peptides is explained in more detail with reference to Table 1 below. Combinations of these peptides, trimmed to 10-20 amino acids in length as appropriate, can also be included in the vaccine compositions of the invention. The combined peptides are preferably joined by one or more linkers as defined herein.

The Aβ-derived peptide antigen is displayed on the surface of the liposome. This is typically by insertion into the outer surface of the liposome. Insertion into the outer surface of the liposome may be facilitated through attachment of the Aβ-derived peptide antigen to a moiety that inserts into the outer surface of the liposome. The liposome may be any liposome that is suitable to present the Aβ-derived peptide antigen on the surface and also encapsulate a peptide comprising a universal T-cell epitope. Typically, the moiety comprises a hydrophobic moiety to ensure insertion into the lipid bilayer of a liposome. The moiety may be any suitable moiety but is preferably a fatty acid. The fatty acid may comprise a palmitoyl residue. A preferred construction, as in ACI-24, comprises the Aβ-derived peptide antigen (Aβ(1-15) in ACI-24) attached to two palmitoyl residues in the N and C terminal regions of the peptide. Thus, the peptide antigen is tetrapalmitolyated. This may be facilitated by incorporating two lysine residues in the N and C terminal regions of the Aβ-derived peptide antigen. The lysine residues are palmitoylated.

In some embodiments, the liposome has a negative surface charge; the liposome is anionic. Preferably, the liposome comprises phospholipids and even more preferably, the phospholipids comprise dimyrsitoylphosphatidyl-choline (DMPC) and dimyrsitoylphosphatidyl-glycerol (DMPG). The liposome may further comprise cholesterol. The molar ratios of these three components may be 9:1:7 in some embodiments.

A most preferred construction therefore comprises the Aβ-derived peptide antigen reconstituted in the liposome. Accordingly, these compositions of the invention may generally be referred to herein as "liposomal vaccine compositions of the invention".

The Aβ-derived peptide antigen induces a B-cell response in the subject. It is a "B-cell antigen". As already explained, Aβ plaques are formed by the 39 to 43 amino acid long Aβ peptide, which is in random coil conformation in its natural non-pathological form. During the transition to the pathological state, it transforms mainly into a β-sheet secondary structure, spontaneously aggregating into insoluble deposits. The Aβ-derived peptide antigen is thus defined herein as a peptide antigen derived from the (maximum of) 43 amino acids of Aβ, but is not full length A. More specifically, the Aβ-derived peptide antigen includes the immunodominant B-cell epitope of Aβ(1-42) but lacks the T-cell epitope found in Aβ(1-42). In some embodiments, the Aβ-derived peptide antigen therefore comprises, consists essentially of or consists of from 13 to 15 contiguous amino acids from the N-terminal 17 amino acids of A. It should be noted that the Aβ-derived peptide antigen may be provided in the context of a larger peptide molecule, the remainder of which is not derived from the Aβ amino acid sequence. For example, the peptide can include additional residues, such as lysine residues to facilitate palmitoylation. Those residues are typically found at the N and C terminus of the peptide. In this context, the term "consists essentially of" means that the Aβ-derived peptide antigen includes the 13 to 15 contiguous amino acids from the N-terminal 17 amino acids of Aβ but can include a limited number of additional residues, such as four lysine residues to facilitate palmitoylation. A preferred Aβ-derived peptide antigen comprises, consists essentially of or consists of amino acids 1-15 of Aβ, which may be referred to as "Aβ(1-15)" (WO2007/068411, ACI-24).

The Aβ-derived peptide antigen included in the compositions of the invention adopts a secondary structure that replicates a pathological form of A. Preferably, the Aβ-derived peptide antigen adopts a secondary structure comprising a β-sheet conformation. Even more preferably, the Aβ-derived peptide antigen adopts a predominantly β-sheet conformation when displayed on the surface of the liposome.

The compositions of the invention typically comprise at least one adjuvant. In some embodiments of the invention, the compositions of the invention comprise two adjuvants. The purpose of the adjuvant(s) is to increase or stimulate the immune response in the subject. Preferably, the at least one adjuvant is part of the carrier (as opposed to being encapsulated within the carrier). Thus, the at least one adjuvant may form part of a liposome; it may form part of the lipid bilayer. The adjuvant may therefore be a lipid-based adjuvant. The adjuvant may be, at least in part, displayed on the surface of the liposome; this may be as a consequence of the adjuvant forming part of the lipid bilayer. One or more adjuvants forming part of a liposome may be combined with an encapsulated adjuvant in some embodiments. In other embodiments, one or more adjuvants forming part of a liposome may be mixed with a further adjuvant (such as Alum or CpG) when forming the liposomes. The carrier (liposome) may function as an adjuvant with the addition of monophosphoryl lipid A (MPLA), which term encompasses MPLA-derivatives such as Monophosphoryl Hexa-acyl Lipid A, 3-Deacyl (Synthetic) (3D-(6-acyl) PHAD®), PHAD® (Phosphorylated HexaAcyl Disaccharide), MPL, to the liposome. Thus, according to particular embodiments, the compositions further comprise MPLA. The MPLA is typically added during liposomal formation (as explained further herein). Preferred liposomes thus comprise dimyrsitoylphosphatidyl-choline (DMPC), dimyrsitoylphosphatidyl-glycerol (DMPG), cholesterol and MPLA. The molar ratios of these four components may be 9:1:7:0.05 in some embodiments.

Other adjuvants that may be employed according to the invention include aluminium hydroxide (Alum) and/or CpG amongst others.

The vaccine compositions of the invention are administered to subjects in order to treat, prevent, induce a protective immune response against or alleviate the symptoms associated with an amyloid-beta associated disease or condition or a condition characterised by, or associated with, loss of cognitive memory capacity. The vaccine compositions can thus have both prophylactic and therapeutic applications. The subject is a mammal and typically a human.

The amyloid-beta associated disease or condition may be a neurological disorder such as Alzheimer's Disease (AD). Other examples of amyloid-beta associated diseases or conditions according to the invention include mild cognitive impairment (MCI), Down('s) syndrome, cardiac amyloidosis, cerebral amyloid angiopathy (CAA), multiple sclerosis, Parkinson's disease, Lewy body dementia, ALS (amyotrophic lateral sclerosis), Adult Onset Diabetes, inclusion body myositis (IBM), ocular amyloidosis, glaucoma, macular degeneration, lattice dystrophy and optic neuritis. Many of these conditions are characterized by, or associated with, loss of cognitive memory capacity. Conditions characterized by, or associated with, loss of cognitive memory capacity according to the invention therefore include AD, mild cognitive impairment (MCI), Down('s) syndrome, cardiac amyloidosis, cerebral amyloid angiopathy (CAA), multiple sclerosis, Parkinson's disease, Lewy body dementia, ALS (amyotrophic lateral sclerosis) and inclusion body myositis (IBM).

Accordingly, the invention provides a method of treating, preventing, inducing a protective immune response against or alleviating the symptoms associated with an amyloid-beta associated disease or condition or a condition characterised by, or associated with, loss of cognitive memory capacity in a subject, the method comprising administering a vaccine composition of the invention to the subject.

Such methods may also be expressed in the form of a medical use of the vaccine compositions of the invention. Accordingly, the invention also provides a vaccine composition of the invention for use in treating, preventing, inducing a protective immune response against or alleviating the symptoms associated with an amyloid-beta associated disease or condition or a condition characterised by, or associated with, loss of cognitive memory capacity in a subject.

Similarly, the invention provides for the use of the vaccine compositions of the invention in the manufacture of a medicament for use in treating, preventing, inducing a protective immune response against or alleviating the symptoms associated with an amyloid-beta associated disease or condition or a condition characterised by, or associated with, loss of cognitive memory capacity in a subject.

All embodiments herein apply to such methods or medical uses, however expressed. Administration of a vaccine composition of the invention to the subject results in the production of, typically polyclonal, IgG antibodies that bind to pathological forms of A. As already explained, those pathological forms of Aβ comprise β-sheet multimers. The antibodies produced may therefore be termed "Aβ-specific" antibodies.

The ability of an antibody to bind the target antigen is mainly regulated by two parameters: affinity and avidity. Affinity of an antibody measures the strength of the monovalent interaction between an antibody and its antigen. Antibody avidity includes the strengthening of binding through more than one point of interaction between an antigen and antibody. The binding ability of polyclonal sera, induced by a vaccination, relies upon both of the above-mentioned parameters (Siegrist, 2013). It is generally termed the avidity of the polyclonal response as it is very difficult to evaluate affinity and avidity independently. As explained in further detail herein, see Example 4 (section 4.2), the inventors have developed an ELISA assay in which the overall binding of sera containing polyclonal antibodies to a lower and higher concentration of antigen is evaluated in parallel (Martineau, 2010). The ratio between the low and high coating signal (the signal represents the concentration of bound antibody) is expressed as the avidity index. A higher index score (closer to 1) indicates an improved overall binding strength, as compared to a lower index score (closer to 0). An increase in the avidity index over time provides an indication of an overall avidity maturation of the vaccine-induced antibodies. It is shown herein (see Example 4 and FIG. 4) that immunization using vaccine compositions of the invention, which comprise an encapsulated peptide containing a universal T-cell epitope, produces an improved maturation effect compared with immunization using ACI-24 (no encapsulated peptide containing a universal T-cell epitope).

The vaccine compositions of the invention may be administered to the subject by any appropriate route of administration. As the skilled person would be aware, vaccine compositions may be administered by topical, oral, rectal, nasal or parenteral (such as intravenous, intradermal, subcutaneous, or intramuscular) routes. In addition, vaccine compositions may be incorporated into sustained release matrices such as biodegradable polymers, the polymers being implanted in the vicinity of, or in close proximity to, where delivery is desired. However, in preferred embodiments, the vaccine composition is administered intramuscularly or subcutaneously.

The vaccine compositions of the invention can be administered a single time to the subject to generate a protective immune response. However, in some embodiments, the vaccine compositions of the invention are administered multiple times to the same subject. Thus, so-called prime-boost regimens may be employed according to the invention. Administration of the vaccine is typically separated by an intervening period of at least 1 week and often around 1-12 months. Without wishing to be bound by a specific hypothesis, it is likely that the addition of a universal T cell epitope to ACI-24 enhances the anti-Aβ antibody response by providing the second signal from activated T-cells specific for the cognate T-cell epitope. The vaccine compositions of the invention represent a powerful new therapeutic option for prevention and treatment of amyloid-beta associated disease or condition such as AD. In some embodiments, the same vaccine composition is administered each time—a homologous vaccination regimen. Homologous vaccination refers to an immunization regimen using the same vaccine for both the prime (first immunization) and boost (second or any further immunization).

On the other hand, heterologous prime-boost immunization requires that a different vaccine is used in the primary and in at least some of the follow up immunizations. In some embodiments, the vaccine compositions of the invention are administered multiple times to the same subject in heterologous prime-boost combination with other "anti-Aβ" vaccines carrying peptide antigens derived from any portion of the Aβ protein, which may include peptide antigens derived from outside the Aβ(1-15) region. In some embodiments, the vaccine compositions of the invention are administered multiple times to the same subject in heterologous prime-boost combination with other "anti-Aβ" vaccines carrying the same peptide antigens as are included in the liposomal vaccine compositions of the invention, which may comprise Aβ(1-15) peptide antigens. In some embodiments, the vaccine compositions of the invention, preferably comprising Aβ(1-15) peptide antigens is administered multiple times to the same subject in heterologous prime-boost combination with other "anti-Aβ" vaccines carrying corresponding Aβ-derived peptide antigens, preferably Aβ(1-15) peptide antigens. Examples of "anti-Aβ" vaccines which could be administered in the heterologous prime-boost vaccination together with the vaccine compositions of the invention comprising Aβ-derived antigens include, but are not limited to, Aβ(1-15)-PADRE vaccine (Agadjanyan et al., 2005; Ghochikyan et al., 2006), Aβ(1-15)-diphtheria toxoid (DT) or CRM vaccine (WO2010016912), tandem repeat of lysine linked Aβ(1-15) (Maier et al., 2006), dendrimeric Aβ(1-15) vaccine (Seabrook et al., 2006), Aβ(1-15) DT conjugate (Liu et al. 2013), Aβ(1-6) coupled to bacteriophage Qβ coated protein (Windblad et al. 2012), Aβ(1-7)-CRM (Arai et al. 2015), Nterm Aβ-KLH (Schneeberger et al 2010).

The invention further provides kits containing vaccine compositions according to the invention. Accordingly, there is provided a kit for treating, preventing, inducing a protective immune response against or alleviating the symptoms associated with an amyloid-beta associated disease or condition or a condition characterised by, or associated with, loss of cognitive memory capacity in a subject comprising a (liposomal) vaccine composition of the invention as described herein. Such kits may be provided with suitable instructions for use. The instructions for use may explain the administration schedule for the compositions. The kits may therefore comprise multiple (separate) doses of the vaccine compositions of the invention. The instructions for use may further explain the storage conditions for the compositions, particularly during the time period between administration of the doses of the vaccine compositions. These kits may be applied to all relevant methods of the invention as disclosed herein.

The invention further provides methods for producing liposomal vaccine compositions of the invention. Such methods may comprise the following steps:
    a. Generating a lipid film
    b. Rehydration of the lipid film in a buffer comprising a peptide comprising a universal T-cell epitope
    c. Generating liposomes from the rehydrated lipid film which encapsulate the peptide comprising a universal T-cell epitope to form a solution containing liposomes that comprise an encapsulated universal T cell epitope
    d. Adding a β-amyloid (Aβ)-derived peptide antigen to the solution and maintaining the solution under conditions resulting in insertion of the β-amyloid (Aβ)-derived peptide antigen into the lipid bilayer of the liposomes.

Such methods are exemplified herein, which details may be applied to these aspects of the invention. In general terms, the methods may involve thin-lipid film formation followed by homogenization and extrusion. Thus, in some embodiments, the lipid film is produced by dissolving the lipid in ethanol and then evaporating the ethanol under vacuum. Preferred lipid components are explained in relation to the liposomal vaccine compositions of the invention and include DMPC, DMPG, cholesterol and MPLA (as adjuvant). Molar ratios of these components may be 9:1:7:0.05. Such molar ratios are also applicable to the liposomal vaccine compositions of the invention. The lipid components may need to be solubilised at an elevated temperature. The elevated temperature may be between 40° C. and 80° C. such as around 60° C.

In step b, the buffer used for rehydration may depend upon which peptide comprising a universal T-cell epitope is employed. Generally, any suitable buffer may be employed. In some embodiments, the buffer comprises sodium acetate or PBS. If SAT42 is to be encapsulated the buffer may be sodium acetate. If any one or more of SAT43, SAT44 or SAT47 is to be encapsulated the buffer may be PBS. In all cases DMSO, such as 5% DMSO, may be added to the buffer. Rehydration may be performed with stirring of the sample.

In step c, the liposomes may be generated by vortexing in the presence of beads. Any suitable beads may be used. The beads may be glass beads for example. This step may produce multilamellar vesicles which are subsequently converted into liposomes comprising a lipid bilayer. This conversion may rely upon several, such as 5-15, preferably 10, freeze-thaw cycles. The freeze-thaw cycles may be followed by homogenization. This may be followed by size based extrusion. In some embodiments, the liposomes are extruded through pores of around 0.08-0.1 µm diameter (or maximum dimension). This may be through a membrane such as a polycarbonate membrane. Extruded liposomes may be concentrated, for example using a form of filtration such as ultrafiltration.

Step d results in insertion of the β-amyloid (Aβ)-derived peptide antigen into the lipid bilayer of the liposomes. The necessary conditions may comprise stirring for 10-60 minutes, such as around 30 minutes at a temperature of 25-35° C., such as around 30° C. The preferred β-amyloid (Aβ-derived peptide antigen is the tetrapalmitoylated peptide comprising Aβ1-15. This peptide includes two lysine residues at either end to produce the tetrapalmitoylated peptide. The peptide may be pre-dissolved in disodium hydrogen phosphate before being injected into the liposomal solution.

The method may further comprise, as a final step, filtering the vaccine composition. This may be under sterile conditions. Filtration may be through a membrane of pore size 0.2 µm. Suitable membranes include polyethersulfone (PES) membranes which may be provided in the form of a syringe filter. The produced vaccine composition may then be stored in suitable conditions until use, such as under refrigeration (e.g. at around 5° C.).

Alternative methods for producing liposomal vaccine compositions of the invention may rely upon crossflow injection, as exemplified herein. Accordingly, the invention further provides methods for producing liposomal vaccine compositions of the invention by crossflow injection. These methods may be particularly applied to compositions encapsulating SAT44 or SAT47. Such methods may comprise the following steps:
  a. Dissolving the lipids (and adjuvant, if lipid based) that form the liposome in solution
  b. Dissolving the peptide comprising a universal T-cell epitope in solution
  c. Mixing the solutions from steps a. and b. using a crossflow injection module to form intermediate liposomes which encapsulate the peptide comprising a universal T-cell epitope
  d. Extruding the intermediate liposomes through a membrane to reduce their size and polydispersity
e. Mixing a solution comprising a β-amyloid (Aβ)-derived peptide antigen with the solution from step d using a crossflow injection module, resulting in insertion of the β-amyloid (Aβ-derived peptide antigen into the lipid bilayer of the liposomes.

Such methods are exemplified herein, which details may be applied to these aspects of the invention. In general terms, the methods use crossflow injection to encapsulate the peptide comprising a universal T-cell epitope and to insert the β-amyloid (Aβ-derived peptide antigen into the lipid bilayer of the liposomes.

In step a, the lipids (which may comprise an adjuvant such as a MPLA adjuvant as described herein) are typically dissolved in ethanol. The ethanol may be 90-100% ethanol, such as 96% ethanol. Dissolving may be accelerated by heating, for example to a temperature between 40 and 80° C., such as around 60° C. Preferred lipid components are explained in relation to the liposomal vaccine compositions of the invention and include DMPC, DMPG, cholesterol and MPLA (as adjuvant). Molar ratios of these components may be 9:1:7:0.05. Such molar ratios are also applicable to the liposomal vaccine compositions of the invention.

In step b, the peptide comprising a universal T-cell epitope is dissolved. The peptide may be dissolved in a suitable buffer (such as His-sucrose buffer) with the aid of agitation, such as sonication, in some embodiments.

In step c, the solutions from steps a and b are mixed using a crossflow injection module to form intermediate liposomes which encapsulate the peptide comprising a universal T-cell epitope. Prior to this step, the solutions from steps a and b may be filtered. A suitable pore size for the filter may be around 0.2 μm. The solutions may be used at any suitable concentration. Once filtered, the solutions may be heated to a temperature between 30 and 60° C., such as around 40° C. Liposomes are formed by injecting the two solutions (from step a and b) through a crossflow module (where the 2 solutions meet). This is generally performed at a specific flow rate and temperature, as would be readily understood by the skilled person (suitable temperatures are mentioned above). In some embodiments, following liposome formation a buffer may be added, typically to reduce ethanol concentration. Any suitable buffer may be used such as a His-sucrose buffer.

In step d the intermediate liposomes are extruded through a membrane to reduce their size and polydispersity. The formed liposomes in solution encapsulate the peptide comprising a universal T-cell epitope. Any suitable membrane can be used. A suitable pore size may be around 100 nm. A suitable membrane type is a polycarbonate membrane. This step may be performed at any suitable temperature, preferably at room temperature (e.g. around 25° C.). Following this step, a filtration step, such as ultra/diafiltration, may be performed to remove ethanol. Any suitable membrane may be employed for this step, such as a hollow fibre membrane with a molecular weight cut off of around 500 kD. A buffer exchange step may be performed into a dispersion buffer. A preferred dispersion buffer is PBS. The PBS may be at a suitable pH, such as between 6 and 8, in particular around 6.9. This may require between 5 and 15, such as around 10, volume exchanges. Prior to step e the liposomes may be diluted in the dispersion buffer to a desired concentration.

The desired concentration may be in the region of 0.1-10 mg/ml, such as around 1 mg/ml. Prior to step e the liposome-containing solution may be heated to a suitable temperature, such as between 30 and 60° C., preferably around 35° C.

Step e involves mixing a solution comprising a β-amyloid (Aβ)-derived peptide antigen with the solution from step d using a crossflow injection module. As discussed herein, the β-amyloid (Aβ-derived peptide antigen is preferably lipidated (e.g. tetrapalmitoylated), which discussion applies mutatis mutandis. Prior to mixing, the β-amyloid (Aβ-derived peptide antigen is typically dissolved in a suitable buffer solution, such as a 10% w/v solution of Beta-OG in 10 mM Na2HPO4 pH 11.4 buffer. The solution is typically heated to a suitable temperature, for example a temperature between 30 and 80° C., such as around 60° C. The solution may be further diluted as needed to ensure a suitable concentration of β-amyloid (Aβ)-derived peptide antigen. A suitable concentration may be in the region of 0.1-10 mg/ml, such as around 1 mg/ml. The pH is typically kept in the range of 11-12, such as around 11, preferably 11.4. Mixing the solution comprising a β-amyloid (Aβ)-derived peptide antigen with the solution from step d using a crossflow injection module results in insertion of the β-amyloid (Aβ)-derived peptide antigen into the outer lipid bilayer of the liposomes. The mixture may be incubated for a fixed period of time at a suitable temperature in order to facilitate insertion of the β-amyloid (Aβ-derived peptide antigen into the lipid bilayer of the liposomes. A suitable period of time may be in the region of 20-120 minutes, such as around 30 minutes.

A suitable temperature may be between 30 and 60° C., preferably around 35° C. The incubation may be performed with agitation, such as stirring.

Following step e, the product can be recovered for inclusion in the compositions of the invention. The product may thus be formulated into a liposomal vaccine composition of the invention. This may involve an ultra/diafiltration step in order to remove the Beta-OG from the buffer solution. Any suitable membrane may be employed for this step, such as a hollow fibre membrane with a molecular weight cut off of around 500 kD. The ultra/diafiltration may involve a buffer exchange step into a final buffer. A preferred final buffer is a His-sucrose buffer, which may be 10 mM Histidine, 250 mM Sucrose. This may require between 5 and 15, such as around 10, volume exchanges. A concentration step may be performed to achieve a preferred final volume. A final (sterile) filtration step may also be performed. This may employ a cartridge filter. The filtration step may be through a filter with any suitable pore size, such as around 0.2 µm. Filtration may be under sterile conditions. The produced vaccine composition may then be stored in suitable conditions until use, such as under refrigeration (e.g. at around 5° C.).

Figure 1A:
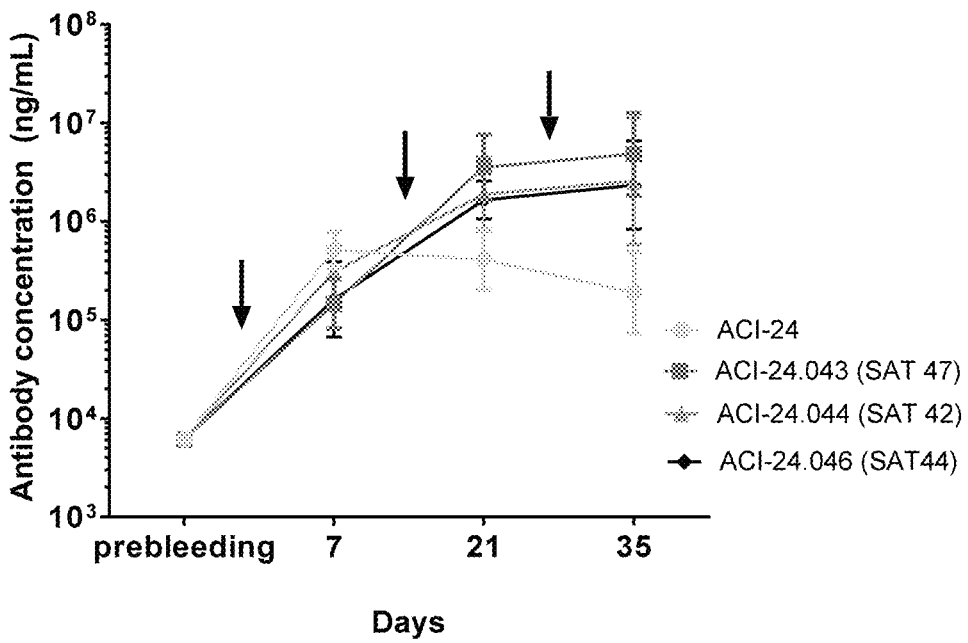
FIG. 1A. Analysis of Aβ1-42-specific IgG antibodies by ELISA in the plasma of C57BL/6 mice 21 (ACI-24.046) or 7 days (ACI-24, ACI-24.043, ACI-24.044) before (prebleeding) and 7, 21 and 35 days after $1^{st}$ immunization with indicated vaccines (arrows indicate the immunization time points). Results are expressed as geometric mean+/−95% confidence interval (CI) of ng/mL with n=5 mice per group. The X axis indicates the days of treatments/bleedings while the Y axis indicates the antibody titers expressed by ng/mL.
Figure 1B:
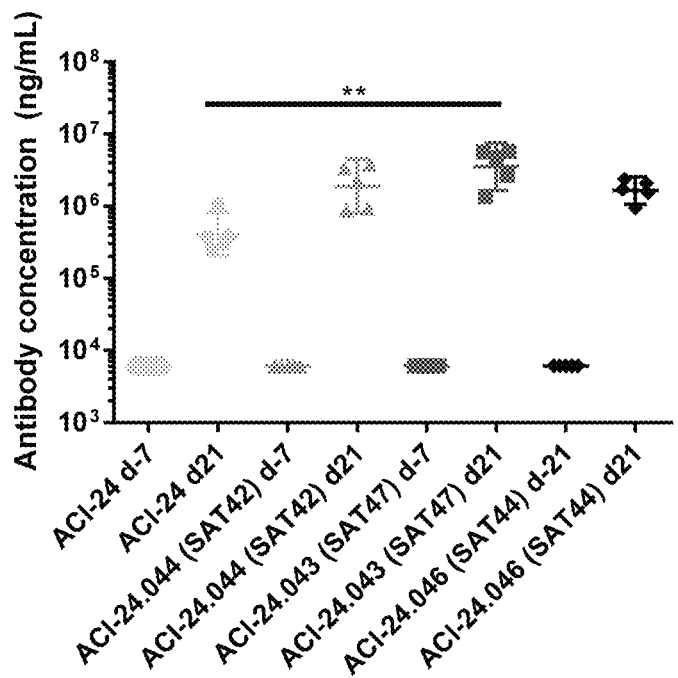
FIG. 1B. Analysis of Aβ1-42-specific IgG antibodies by ELISA in the plasma of C57BL/6 mice 21 (ACI-24.046) or 7 (ACI-24, ACI-24.043, ACI-24.044) days before (prebleeding) and 21 days after $1^{st}$ immunization with indicated vaccines. Results are expressed as geometric mean+/−95% CI of ng/mL with 5 mice per group. Statistical test among different groups at day 21: Kruskal-Wallis test with Dunn's multiple comparisons. * p<0.05; ** p<0.01. The X axis indicates the individual plasma from groups immunized with indicated vaccines while the Y axis indicates the antibody titers expressed by ng/mL.

| Table of abbreviations | |
|---|---|
| ABTS | 2,2'-azino-bis(3-ethylbenzothiazoline-6-sulphonic acid) |
| Aβ | Amyloid beta (abeta) |
| Ac2O | Acetic anhydride |
| AD | Alzheimer's Disease |
| AP | Alkaline phosphatase |
| APC | Antigen Presenting Cells |
| BSA | Bovine Calf Serum |
| AU/mL | Arbitrary Units per mL |
| CI | Confidence Interval |
| DMF | Dimethylformamide |
| DMPC | 1,2-Dimyristoyl-sn-glycero-3-phosphocholine |
| DMPG | 1,2-Dimyristoyl-sn-glycero-3-phosphorylglycerol |
| DMSO | Dimethyl sulfoxide |
| ELISA | Enzyme-linked immunosorbent assay |
| HLA | Human leukocyte antigen |
| HPLC | High-performance liquid chromatography |
| HRP | Horseradish peroxidase |
| Ig | Immunoglobulin |
| KLH | Keyhole limpet hemocyanin |
| MPLA | Monophosphoryl Lipid A |
| MS | Mass spectrometry |
| MSD | Meso Scale Discovery |
| Pal1-15 | Tetrapalmitoylated Aβ1-15 |
| PBS | Phosphate buffered saline |
| PES | Polyethersulfone |
| pNPP | p-nitrophenyl phosphate |
| s.c. | Subcutaneous |
| TMB | Tetramethylbenzidine |
| TFA | Trifluoroacetic acid |
| TIS | Triisopropylsilane |
| TLR4 | Toll-like receptor 4 |
| Beta-OG | n-Octyl-β-D-Glucopyranoside |

The invention will be further understood with reference to the following non-limiting examples:

Example 1. Design of New T-Cell Epitopes

The ability of a T-cell epitope to activate T cells (immunogenicity score) is the result of two complementary properties: i) affinity to HLA and ii) capacity to bind different HLA haplotypes in a promiscuous manner. An in silico evaluation (Epivax) of several T-cell epitopes from different origins was performed with the objective of selecting the peptides with the highest immunogenicity score. In a preliminary phase, 10 different peptides from different origins (Keyhole limpet hemocyanin-KLH, Diphtheria toxin, Influenza virus, Epstein Barr virus and Herpes virus) were evaluated. Peptides with the best immunogenicity score (higher than 10) were selected due to their chance to be highly immunogenic in humans based on their predicted HLA affinity and HLA haplotype coverage (selected peptide sequences are shown in Table 1).

TABLE 1

| Name | Sequence | Peptide origin |
|---|---|---|
| SAT6 | STLEYFLYDPIFFLHHSNTDRLWAIWQAL QKYRGKPYNTANCAIVRHDTY (SEQ ID NO: 5) | KLH |
| SAT13 | VHHNTEEIVAQSIALSSLMV (SEQ ID NO: 6) | Diphtheria Toxin |
| SAT15 | IDGVKLESMGVYQILAIYSTVASSL (SEQ ID NO: 7) | Influenza hemagglutinin |
| SAT17 | VYGGSKTSLYNLRRGTALAI (SEQ ID NO: 8) | Epstein Barr Virus |

Following the screening results of the individual peptides, the combined promiscuous peptides composed of 2 or 3 immunogenic T-cell epitopes from different origins (named SAT42, SAT43 and SAT44) and the promiscuous peptides composed of trimmed peptides (e.g. SAT47 and SAT43) were designed (Table 2). The trimmed peptides were designed by selecting, in the sequence of each individual T-cell epitope, the most immunogenic 15-mer peptide sequence, based on the in silico predicted T-cell epitope hotspots. The goal was to increase the immunogenicity score without increasing the size of the final promiscuous peptide, due to peptide synthesis and vaccine encapsulation process constraints. In brief, the peptide synthesis yield and success rate is lowered upon increasing the length of the peptides, especially above 30 amino acids in length, and in addition they are composed mainly of hydrophobic residues, as for T-cell epitope peptides disclosed herein. In addition, the peptide encapsulation rate is lowered with the increasing length of the peptide, as the chances to accommodate it in the lumen of the liposomes are decreased as peptide length increases. The in silico immunogenicity score of these 4 promiscuous T-cell epitopes was very high and, importantly higher than that of the individual component peptides, therefore confirming that combining peptides from different origins can improve HLA affinity and HLA haplotype coverage (promiscuous T cell epitope sequences are shown in Table 2).

TABLE 2

| Name | Sequence | Peptide design | Peptide origin |
|---|---|---|---|
| SAT42 | VHHNTEEIVAQSIALSSLMVPMGA PQYIKANSKFIGITEL (SEQ ID NO: 1) | SAT13 + PMGAP+ Tetanus toxin | Diphtheria Toxin + Tetanus toxin |
| SAT43 | VYGGSKTSLYNLRRGTALAIVVRQ YIKANSKFIGITELVVRPIFFLHHSN TDRLWAI (SEQ ID NO: 2) | SAT17 + VVR+ Tetanus toxin + VVR + SAT6 | Epstein Barr + Tetanus + KLH |
| SAT44 | VYGGSKTSLYNLRRGTALAIVVRQ YIKANSKFIGITEL (SEQ ID NO: 3) | SAT17 + VVR + Tetanus toxin | Epstein Barr + Tetanus |
| SAT47 | SMGVYQILAIYSTVVRIVAQSIALSS VVRYIKANSKFIGVVRLYNLRRGTA L (SEQ ID NO: 4) | SAT15 + VVR + SAT 13 + VVR + Tetanus + VVR + SAT17 | Influenza hemagglutinin + Difteria + Tetanus + Epstein Barr |

Example 2. Vaccine Synthesis and Formulation

General Method of Universal T-Cell Epitope Peptide Synthesis and Purification

T-cell peptides were manufactured by linear solid phase peptide synthesis (SPPS) on 2-Chlorotrityl resin using standard Fmoc chemistry. Standard coupling procedure was performed using 3.0 equivalent of amino acid and coupling reagent in the presence of 3.0 equivalent of base in DMF for 1 hour at room temperature. For difficult coupling sequences double coupling was implemented with extended reaction time. After the completion of the amino acid coupling, an acetylation capping step was introduced using 5.0 equivalent of Ac2O in pyridine to abort the undesired peptide chain elongation. The resin was washed with DMF and Fmoc group was removed by using 20% piperidine in DMF for 5 min. After finishing the SPPS, global deprotection and peptide cleavage from the resin was done using standard cleavage cocktail (TFA/TIS/water) for 2 hours at room temperature. The resin was filtered off and washed with TFA. The crude product was subsequently precipitated with 10-fold excess volume of cold isopropyl ether/hexane and the solid was filtered off by using a glass frit and dried under vacuum. The crude peptide was purified on reversed phase C18 column using a gradient of solvent A (water, 0.1% TFA) and solvent B (acetonitrile, 0.1% TFA) on a preparative HPLC system. The HPLC fractions containing desired peptide with purity above 90% were pooled together diluted in water and performed an ion exchange. The desired ion exchange fractions were lyophilized. The identity and purity of final peptide was characterized and confirmed by HPLC-MS analysis.

Preparation of the ACI-24.043/ACI-24.044/ACI-24.045/ACI-24.046/Vaccines (Thin Lipid Film)

The vaccines containing encapsulated T-cell epitopes peptide were produced by thin-lipid film technology followed by homogenization and extrusion. First, by solubilizing DMPC, DMPG (Lipoid, Germany), cholesterol and monophosphoryl hexa-acyl Lipid A, 3-deacyl synthetic or 3D-(6-acyl) PHAD™ (Avanti Polar Lipids, USA) at molar ratios 9:1:7:0.05 in ethanol at 60° C., respectively. Ethanol was evaporated under vacuum rotavapor in order to obtain thin lipid film.

Lipid film was rehydrated with one of these buffers (depending on T-cell epitope peptide to be encapsulated):
  20 mM sodium acetate pH 4 (Fluka), 5% DMSO (Sigma Aldrich) in MilliQ water containing 0.8 mg/mL T-cell epitope peptide SAT42, or
  0.1×PBS pH 7.4, 5% DMSO (all Sigma-Aldrich) in MilliQ water containing 0.3-0.4 mg/mL T-cell epitope peptide SAT43, SAT44 or SAT47.

Solution was gently stirred for 15 minutes. Sample was further vigorously vortexed in the presence of glass beads. Resulting multilamellar vesicles were subjected to 10 freeze-thaw cycles (liquid N2 and waterbath at 37° C.) and submitted to homogenization followed by sequential extrusion through polycarbonate membranes (Whatman, UK) with a pore size of 0.1/0.08 µm. Both homogenization and extrusion steps were performed using EmulsiFlex-C5 (Avestin, Canada). Extruded liposomes were concentrated by ultrafiltration and buffer was exchanged to PBS pH 7.4 by diafiltration (10 times exchange). The resulting liposomes were diluted in PBS pH 7.4 and heated to 30° C. prior to Pal1-15 addition.

A tetrapalmitoylated human peptide Pal1-15 (Bachem AG, Switzerland) was dissolved in 10 mM Na2HPO4, pH 11.4 in MilliQ water with 1% ß-OG (Sigma-Aldrich, USA), injected in the liposomal solution at 30° C. and stirred for 30 minutes followed by concentration steps through ultrafiltration and dilution in PBS pH 7.4 by diafiltration. The resulting liposomes were then sterile filtered by passing through 0.2 µm polyethersulfone (PES) membrane syringe filters and stored at 5° C.

Preparation of the ACI-24.043 Vaccine (Crossflow Injection)

The lipids (DMPG, DMPC, cholesterol and 3D-(6-acyl) PHAD™ (Avanti Polar Lipids, USA)) were dissolved in 96% EtOH in a heating cabinet at 60° C. After complete dissolution of the lipids, the solution was filtered through a 0.2 µm pore size filter into the injection system which was heated to 60° C. In detail, the appropriate amount of ACI-24.043 (SAT47) was dispersed in EtOH at room temperature by the aid of sonication (EtOH concentration is typically 2% v/v of final SAT47 solution). After complete dispersion of the peptide, His-Sucrose buffer (10 mM Histidine, 250 mM Sucrose) was added to achieve a drug to lipid ratio of 1/50 by mass. The SAT47 solution was filtered through a 0.2 µm pore size filter (Sartoscale filter) into the injection buffer bottle which was then heated up to 40° C. Liposomes are formed at the site of injection when the lipid/EtOH solution and the injection buffer mixes. Immediately after liposome formation there was an online dilution step with 10 mM Histidine, 250 mM Sucrose in order to decrease the EtOH concentration. The intermediate liposomes were extruded through 100 nm pore size polycarbonate membranes (1 pass) at RT. Ultra-/diafiltration (UDF) using a hollow fiber membrane (MWCO: 500 kD) was performed to remove EtOH and the buffer was exchanged to PBS pH 6.9 (10 volume exchanges). SAT47 liposomes were then diluted using the dispersion buffer (PBS pH 6.9) to a total lipid concentration of 1 mg/mL and warmed up to 35° C. The Pal1-15 was dissolved in a 10% w/v solution of beta-OG in 10 mM Na2HPO4 pH 11.4 buffer at 60° C. and was further diluted with the same buffer to a final concentration of 1 mg/mL. The pH was adjusted to 11.4. After mixing of these two solutions using a crossflow injection module, the liposomal suspension was further incubated at 35° C. for 30 minutes under stirring to allow complete insertion of Pal1-15. A second UDF step using a hollow fiber membrane (MWCO: 500 kD) was performed to remove beta-OG and to exchange buffer to 10 mM Histidine, 250 mM Sucrose (10 volume exchanges). The product was concentrated in its final volume and filtered through a 0.2 µm Acrodisc mPES syringe filters.

Preparation of the ACI-24.046 Vaccine (Cross Flow Injection)

The lipids (DMPG, DMPC, cholesterol and 3D-(6-acyl) PHAD™ (Avanti Polar Lipids, USA)) were dissolved in 96% EtOH in a heating cabinet at 60° C. After complete dissolution of the lipids, the solution was filtered through a 0.2 µm pore size filter into the injection system which was heated to 60° C. In parallel, ACI-24.046 (SAT44) was dissolved in the injection buffer (10 mM Histidine, 250 mM Sucrose) at 40° C. After complete dissolution of the SAT44, the solution was filtered through a 0.2 µm pore size filter (Sartoscale) into the injection buffer bottle which was heated to 40° C. Liposomes are formed at the site of injection when the lipid/EtOH solution and the injection buffer mixes. Immediately after liposome formation there was an online dilution step with 10 mM Histidine, 250 mM Sucrose in order to decrease the EtOH concentration. The intermediate liposomes were extruded through 100 nm pore size polycarbonate membranes (1 pass) at room temperature. Ultra-/diafiltration (UDF) using a hollow fiber membrane (MWCO:

500 kD) was performed to remove EtOH and the buffer was exchanged to PBS pH 6.9 (10 volume exchanges). SAT44 liposomes were then diluted using the dispersion buffer (PBS pH 6.9) to a total lipid concentration of 1 mg/mL and warmed up to 35° C. The Pal1-15 was dissolved in a 10% w/v solution of beta-OG in 10 mM Na2HPO4 pH 11.4 buffer at 60° C. and was further diluted with the same buffer to a final concentration of 1 mg/mL. The pH was checked and carefully adjusted back to 11.4. After mixing of these two solutions using an injection module, the liposomal suspension was further incubated at 35° C. for 30 minutes under stirring to allow complete insertion of Pal1-15. A second UDF step using a hollow fiber membrane (MWCO: 500 kD) was performed to remove beta-OG and to exchange buffer to 10 mM Histidine, 250 mM Sucrose (10 volume exchanges). The product was concentrated in its final volume and finally filtered through a 0.2 μm Acrodisc mPES syringe filters.

Figure 6A:
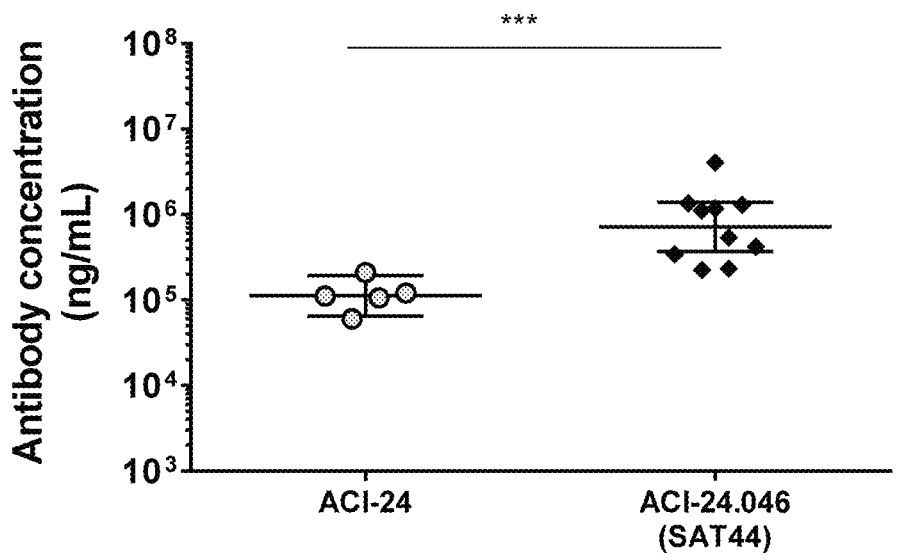
FIGS. 6A-6B. Analysis of Aβ1-42-specific IgG antibodies by ELISA in the plasma of C57BL/6 mice 7 days after the $3^{rd}$ immunization (Day 36) with ACI-24 and ACI-24.046 (SAT44) vaccines (FIG. 6A) or with ACI-24 and ACI-24.043 (SAT47) vaccines (FIG. 6B). Results are expressed as geometric mean+/−95% CI of ng/mL with n=10 mice per group. The X axis indicates the vaccines used for immunization of each particular group, while the Y axis indicates antibody titers expressed in ng/mL. Statistical test: Mann-Whitney test between ACI-24 and the indicated vaccine. * p<0.05;  p<0.01, *p<0.001
Figure 6B:
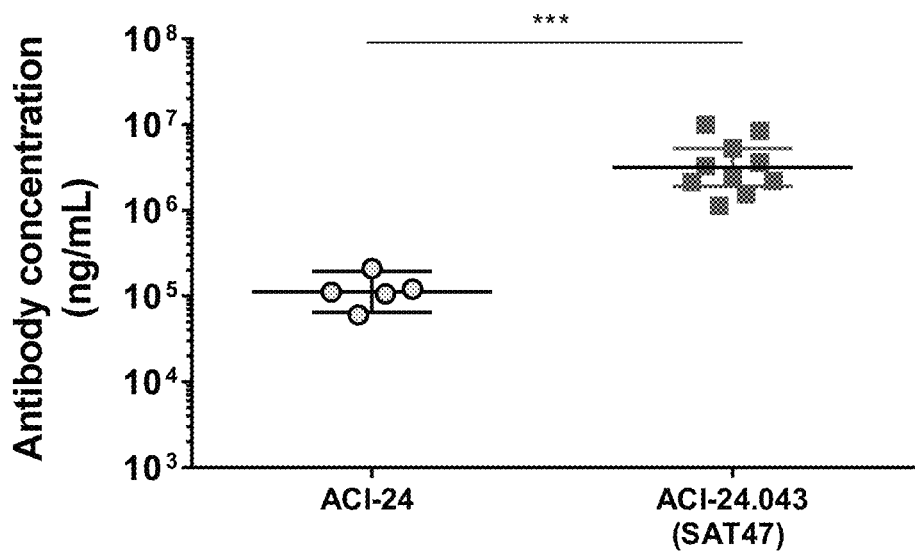

Example 3. Proof-of-Concept (PoC) In Vivo Immunogenicity Studies of Vaccines with Encapsulated T-Cell Epitopes Following the successful encapsulation of different T-cell epitopes, the immunogenicity of vaccines containing encapsulated T-cell epitopes with high immunogenicity score SAT42, SAT44 and SAT47 (ACI-24.044, ACI-24.046 and ACI-24.043 vaccines respectively) in comparison with the ACI-24 vaccine was tested in vivo. Wild type C57BL/6 mice received a total of three subcutaneous (s.c.) immunizations at days 0, 14 and 28 of ACI-24, ACI-24.044 (with encapsulated SAT42), ACI-24.046 (with encapsulated SAT44) and ACI-24.043 (with encapsulated SAT47). Blood samples were collected at day −21 (ACI-24.046) or −7 (ACI-24, ACI-24.043, ACI-24.044) (pre-bleed), 7, 21 and 35 to measure Aβ1-42-specific IgG titers by ELISA.

Plates were coated with 10 μg/ml of human Aβ1-42 peptide film (Bachem, Switzerland) overnight at 4° C. After washing with 0.05% Tween 20/PBS and blocking with 1% BSA/0.05% Tween/PBS, serial dilutions of plasma were added to the plates and incubated at 37° C. for 2 hours. After washing, plates were incubated with alkaline phosphatase (AP) conjugated anti-mouse IgG antibody (Jackson ImmunoResearch, PA, USA) for 2 hours at 37° C. After final washing, plates were incubated for 2.5 hours with AP substrate (pNPP) and read at 405 nm using an ELISA plate reader. Results are expressed by reference to serial dilutions of a commercially available antibody (6E10, Biolegend, UK, Cat. 803002). FIG. 1A shows the Aβ1-42-specific IgG titers induced by ACI-24 vaccine with or without encapsulated T-cell epitope over time. Even though ACI-24 vaccine showed the highest Aβ1-42-specific IgG titers at Day 7, after the 1st immunization, an increase in antibody titers was observed after the $2^{nd}$ and $3^{rd}$ immunization when a T-cell epitope was encapsulated in ACI-24 vaccine. The results in FIG. 1B show that immunization with ACI-24 vaccines comprising encapsulated T-cell epitopes induced an increase of Aβ-specific antibody titers as compared to ACI-24, which reached statistical significance for the group immunized with ACI-24.043 (with encapsulated SAT47) vaccine.

Vaccines with encapsulated SAT42, SAT43, SAT44 or SAT47 were tested in a Cynomolgus monkey study. Four monkeys per group received three monthly s.c. immunizations (Day 1, 29 and 57) with ACI-24.044 (encapsulated SAT 42—two groups with a total of 8 monkeys), ACI-24.046 vaccine (encapsulated SAT 44—2 groups with a total of 8 monkeys), ACI-24.045 vaccine (encapsulated SAT 43—4 monkeys) or ACI-24.043 vaccine (encapsulated SAT 47—4 monkeys). Blood was collected before the first immunization (Day 1) and 1 and 3 weeks after each immunization (Day 8, 22, 36, 50, 64 and 78) to measure Aβ1-42-specific IgG titers by ELISA.

Plates were coated with 10 μg/ml of human Aβ1-42 peptide film (Bachem, Switzerland) overnight at 4° C. After washing with 0.05% Tween 20/PBS and blocking with 1% BSA/0.05% Tween 20/PBS, 8 two-fold serial dilutions of sera were added to the plates and incubated at 37° C. for 2 hours. After the washing, plates were incubated with a horseradish peroxidase (HRP)-conjugated anti-monkey-IgG antibody (KPL, Cat. No. 074 11 021) for 2 hours at 37° C. After washing, plates were incubated with 50 μl of ABTS/H2O2 (2,2'-azino-bis(3-ethylbenzothiazoline-6-sulphonic acid) (HRP substrate) and read at 405 nm after one hour using an ELISA plate reader. Results are expressed by reference to serial dilutions of a positive monkey pool used as standard.

The immunogenicity of vaccines with different T-cell epitopes was compared with ACI-24 vaccine. Table 3 shows the Aβ-specific antibody titer fold increase as compared to ACI-24 vaccine 1 week after the third immunization. All tested vaccines, ACI-24.046 (SAT44), ACI-24.043 (SAT47) ACI-24.045 (SAT43) and ACI-24.044 (SAT42) induced an increase of the antibody titers of at least 7 fold (ACI-24.044 with encapsulated SAT42), as compared to the titers induced by ACI-24 vaccine. ACI-24.043 vaccine (with encapsulated SAT47) and ACI-24.046 (with encapsulated SAT44) induced significantly higher Aβ-specific antibody titers as compared to ACI-24 1 week after the third immunization (Table 3). ACI-24.043 vaccine (with encapsulated SAT47) and ACI-24.046 (with encapsulated SAT44) each have high Epivax scores (142.89 and 57.2 respectively).

TABLE 3

| Aβ-specific antibody titer fold increase as compared to ACI-24 (1 week after the third immunization, Day 64) | | | | |
|---|---|---|---|---|
| Vaccine | ACI-24.046 (encapsulated SAT44) | ACI-24.043 (encapsulated SAT47) | ACI-24.045 (encapsulated SAT43) | ACI-24.044 (encapsulated SAT42) |
| Aβ-specific IgG titer fold increase over ACI-24 | 40<br>p = 0.0027 (**) | 144<br>p = 0.0003 (***) | 17<br>p = 0.1408 (ns) | 7<br>p = 0.6003 (ns) |

Statistical test: Kruskal-Wallis test with Dunn's multiple comparisons.
* p < 0.05;
(**) p < 0.01;
(***) p < 0.001; ns: non significant.

Following the results obtained in vivo (FIG. 1) with the vaccines ACI-24.046 (encapsulated SAT44) and ACI-24.043 (encapsulated SAT47) manufactured according to thin-lipid film technology, we tested the in vivo immunogenicity of the same vaccines manufactured according to a crossflow injection method. Wild type C57BL/6 mice received a total of three subcutaneous (s.c.) immunizations at days 0, 14 and 28 of ACI-24, ACI-24.046 (with encapsulated SAT44) or ACI-24.043 (with encapsulated SAT47) vaccines. Blood samples were collected at days −7, 7, 21 and 35 to measure Aβ1-42-specific IgG titers by ELISA. The results in FIG. 6 show that immunization with ACI-24 vaccines comprising encapsulated T-cell epitopes induced a significant increase of Aβ-specific antibody titers as compared to ACI-24.

Example 4. Quality of Induced Aβ-Specific Antibodies 4.1 In Vitro Inhibition of Human Aβt-42 Self-Association The quality of induced Aβ-specific antibodies was tested in vitro by measuring inhibition of Aβ1-42 self-association/aggregation. This assay is based on the ability of mouse pre- and post-immunization plasma to impair the natural predisposition of human Aβ1-42 to self-associate.

Standard ELISA plates were coated with 1 µg/mL Aβ1-42 overnight at 4° C. Plates were washed 4 times with 300 µL of 0.05% Tween 20/PBS. Saturation was achieved by adding 0.5% BSA/PBS and incubating for 1 hour at 37° C. After washing, four 2-fold serial dilutions of plasma were added to the plates for 20 minutes at room temperature with agitation. Biotinylated Aβ1-42 was added to each well to a final concentration of 0.1 µg/mL and incubated at room temperature for 2 hours with agitation. Biotinylated Aβ1-42 without plasma was used as positive control for Aβ1-42 self-association (considered as 100% of self-association, 0% of inhibition). After a washing step, plates were incubated with a horseradish peroxidase (HRP)-conjugated to streptavidin (R&D Systems, Canada, Ref. 890803) at 1/200 dilution in 0.5% BSA/0.05% Tween 20/PBS for 1 hour at room temperature with agitation. After washing, the plates were incubated with Sure Blue Reserve TMB substrate (Seracare, Cat. 5120-0081) for 10 minutes. The reaction was stopped with Bethyl stop solution (Bethyl Laboratories, Inc, Cat. E115) and plates were read at 450 nm using an ELISA plate reader. The percentage inhibition of self-association was calculated using as reference the biotinylated Aβ1-42 without plasma as positive control (0% inhibition).

Figure 2A:
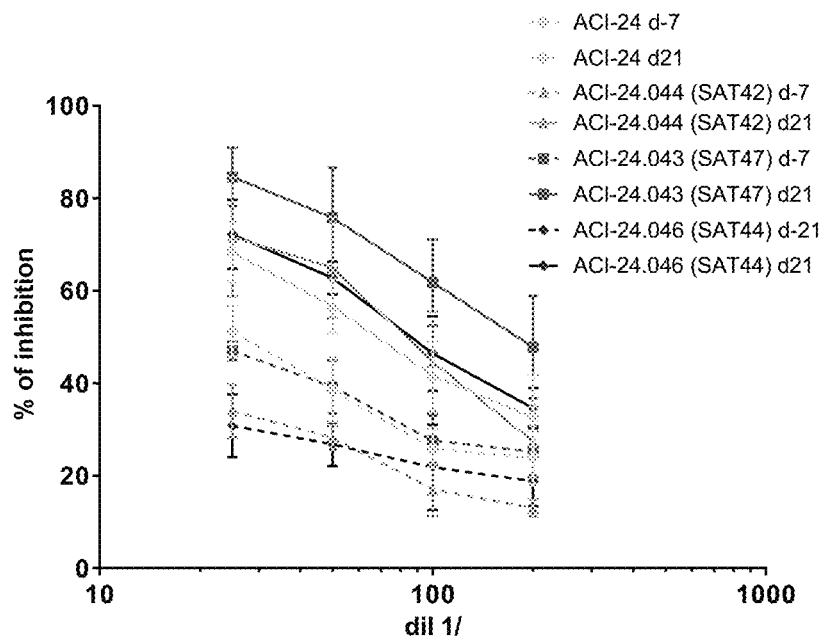
FIG. 2A. Analysis of inhibition of Aβ1-42 self-association by ELISA of IgG antibodies in the plasma of C57BL/6 mice 21 or 7 days before (dotted lines) and 21 days after $1^{st}$ immunization (bold lines) with indicated vaccines. Results are expressed as mean+/−standard deviation of 5 mice per group of the percentage of inhibition of Aβ1-42 self-association. The X axis indicates the serial dilutions of the plasma, while the Y axis indicates the percentage of inhibition of Aβ1-42 self-association.
Figure 2B:
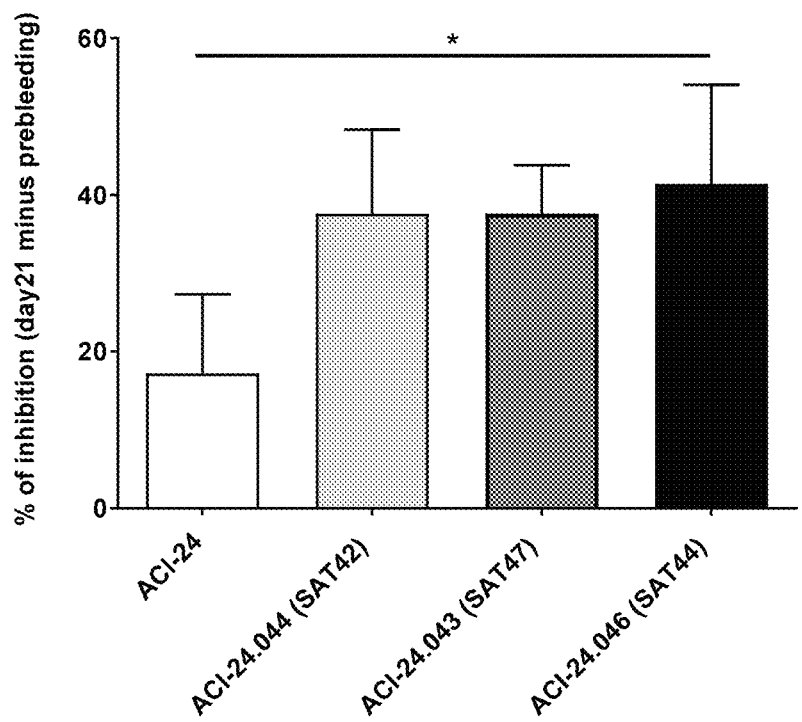
FIG. 2B. Inhibition of Aβ1-42 self-association shown as percentage (%) of inhibition at day 21 minus % of inhibition at day −21 or −7 (background-prebleeding) at 1/25 dilution of the plasma. The X axis indicates the groups treated with indicated vaccines, while the Y axis indicates the percentage of inhibition of Aβ1-42 self-association after subtraction of the background.

The results showed that the Aβ-specific antibodies generated after 2 immunizations with all vaccines containing a T-cell epitope impaired Aβ1-42 self-association more efficiently than antibodies induced by ACI-24 (FIG. 2A). Since the pre-bleeding plasma induces a background inhibition of self-association, the percentage at day 21 was normalized by subtracting the background of the pre-bleeding plasma. The Aβ1-42 specific antibodies generated by immunization with all ACI-24 vaccines containing a T-cell epitope showed higher inhibition of Aβ1-42 self-association as compared to ACI-24; this inhibition reached statistical significance in the group immunized with ACI-24.046 (with encapsulated SAT44) (FIG. 2B).

4.2 Generation of Antibodies Recognizing Aβ Oligomers

In order to evaluate the specificity of induced antibodies in C57BL/6 mice to bind the pathological Aβ, Aβ1-42-oligomers specific IgG responses were determined by ELISA. Plates were coated with 10 µg/ml of oligomers prepared as previously described (Adolfsson, 2012) overnight at 4° C. After washing with 0.05% Tween 20/PBS and blocking with 1% BSA/0.05% Tween 20/PBS, serial dilutions of plasma were added to the plates and incubated at 37° C. for 2 hours. After washing, plates were incubated with alkaline phosphatase (AP) conjugated anti-mouse IgG antibody (Jackson ImmunoResearch, Cat: 115-055-164, PA, USA) for 2 hours at 37° C. After final washing, plates were incubated for 2.5 hours with AP substrate (pNPP) and read at 405 nm using an ELISA plate reader. Results are expressed by reference to serial dilutions of a commercial available antibody (6E10, Biolegend, UK, Cat. 803002).

Figure 3:
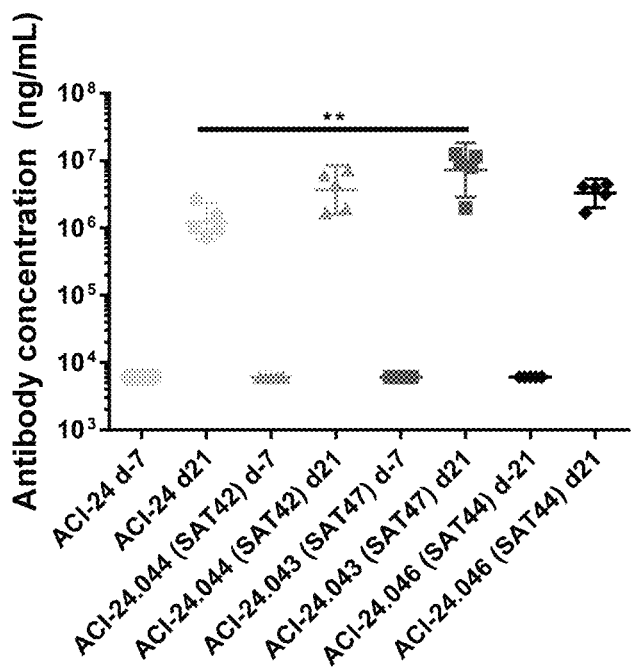
FIG. 3. Analysis of Aβ1-42 oligomer-specific IgG antibodies by ELISA in plasma of C57BL/6 mice 21 (ACI-24.046) or 7 (ACI-24, ACI-24.043, ACI-24.044) days before and 21 days after 1st immunization with indicated vaccines. Results are expressed as geometric mean+/−95% CI of ng/mL with 5 mice per group. Statistical test among groups at day 21: Kruskal-Wallis test with Dunn's multiple comparisons. * p<0.05; ** p<0.01. The X axis indicates the groups immunized with indicated vaccines while the Y axis indicates the antibody titers expressed by ng/mL.

Each sample was tested in eight or four 2-fold serial dilutions, starting at 1/100, 1/400, 1/800 or 1/1600 dilution, based on Aβ1-42 antibody titers. The results in FIG. 3 show that immunization with all ACI-24 vaccines containing a T-cell epitope induced an increase of Aβ1-42 oligomer-specific antibody titers as compared to ACI-24, which reached statistical significance for the group immunized with ACI-24.043 (with encapsulated SAT47) vaccine. The avidity index of induced antibodies in C57BL/6 mice, 7 and 21 days after immunization was determined by ELISA assay. One half of a standard ELISA plate was coated with 10 µg/mL of Aβ1-42 peptide film and the other half with 1 µg/mL of Aβ1-42 peptide film overnight at 4° C. After washing with 0.05% Tween 20/PBS and blocking with 1% BSA/0.05% Tween 20/PBS, eight 2-fold serial dilutions of plasma were added to both coating conditions and incubated at 37° C. for two hours. After a washing step, plates were incubated with alkaline phosphatase (AP)-conjugated anti-mouse IgG antibody (Jackson ImmunoResearch, Cat: 115-055-164, PA, USA) for 2 hours at 37° C. After final washing, plates were incubated for 2.5 hours with AP substrate (pNPP) and read at 405 nm using an ELISA plate reader. Results are expressed by reference to serial dilutions of a commercially available antibody (6E10, Biolegend, UK, Cat. 803002).

For the determination of the avidity index, AU/mL were calculated for each sample on both coatings using the standard curve obtained on 10 µg/mL of Aβ1-42 peptide. O.D. values between 0.6 and 2.8 were used for the back-calculation of the concentration. The avidity index is calculated as a ratio between the antibody concentration on the lower coating concentration (1 µg/mL of Aβ1-42 peptide) and the saturated coating (10 µg/mL of Aβ1-42 peptide).

Figure 4:
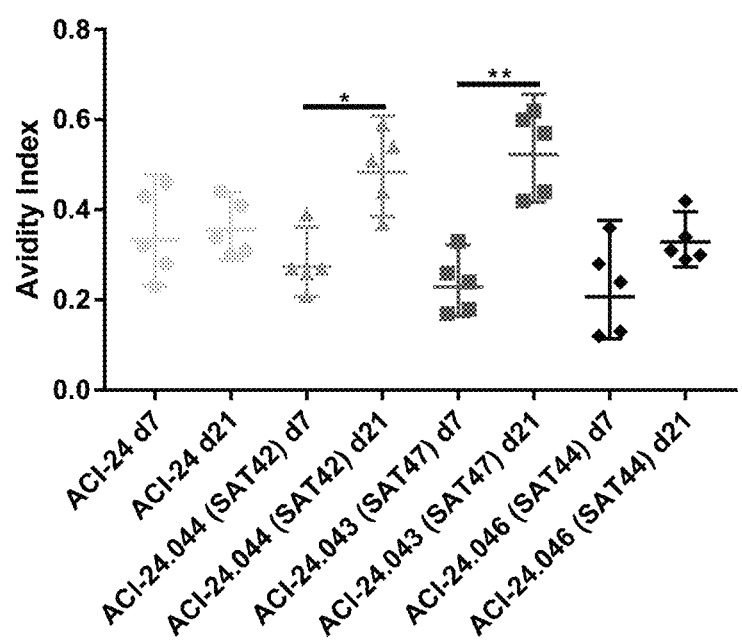
FIG. 4. Analysis of Aβ1-42 avidity of IgG antibodies by ELISA in plasma of C57BL/6 mice 7 and 21 days after 1st immunization with indicated vaccines. Results are expressed as geometric mean+/−95% CI of avidity index with 5 mice per group. Statistical test: Mann-Whitney test between day 7 and day 21 for each group. * p<0.05; ** p<0.01. The X axis indicates the groups immunized with indicated vaccines while the Y axis indicates the avidity index.

The results in FIG. 4 show that immunization with all ACI-24 vaccines containing a T-cell epitope induced an Aβ1-42-specific antibody avidity maturation between the 1st and the $2^{nd}$ immunization (day 7 and day 21 respectively), which reached statistical significance in the groups immunized with ACI-24.044 (with encapsulated SAT42) and ACI-24.043 (with encapsulated SAT47).

In order to evaluate the specificity of induced antibodies in Cynomolgus monkeys to bind the pathological Aβ Aβ1-42 oligomer-specific IgG titers were measured by Meso Scale Discovery (MSD) technology at Day 64 (1 week after the third immunization) in sera of Cynomolgus monkeys immunized with ACI-24.046 (with encapsulated SAT44—2 groups with a total of 8 monkeys), ACI-24.045 vaccine (encapsulated SAT 43—4 monkeys) or ACI-24.043 vaccine (encapsulated SAT 47—4 monkeys). MSD streptavidin plates were saturated over night with 5% of Blocker A (MSD, Ref. R93BA-4) at 4° C. The day after, plates were washed 4 times with 0.05% Tween 20/PBS and coated with 25 µl of capturing antibody biotinylated 6E10 (Biolegend, Ref. 803008) in PBS at 0.5 µg/ml for 1 hour at 37° C. on a shaker. After washing, plates were incubated with 25 µl of Aβ1-42 oligomers (Adolfsson, 2012) at 10 µg/ml in PBS for 1 hour at 37° C. on a shaker. Plates were washed and incubated with eight 2-fold dilutions of monkey sera (starting dilution 1/50 in 1% Skim milk/0.05% Tween/PBS). Samples were incubated 2 hours at 37° C. on a shaker. Plates were washed 4 times and anti-human IgG detection antibody labeled with SULFO-TAG (Jackson, Ref. 109-005-098) was added, diluted in 1% Skim milk/0.05% Tween 20/PBS for 1 hour at 37° C. on a shaker. After 4 washes, MSD read buffer T 2X (MSD, Ref. R92TC-2) was added and plates were read within 5 minutes. Results are expressed by reference to serial dilutions of monkey pool used as standard.

Figure 5:
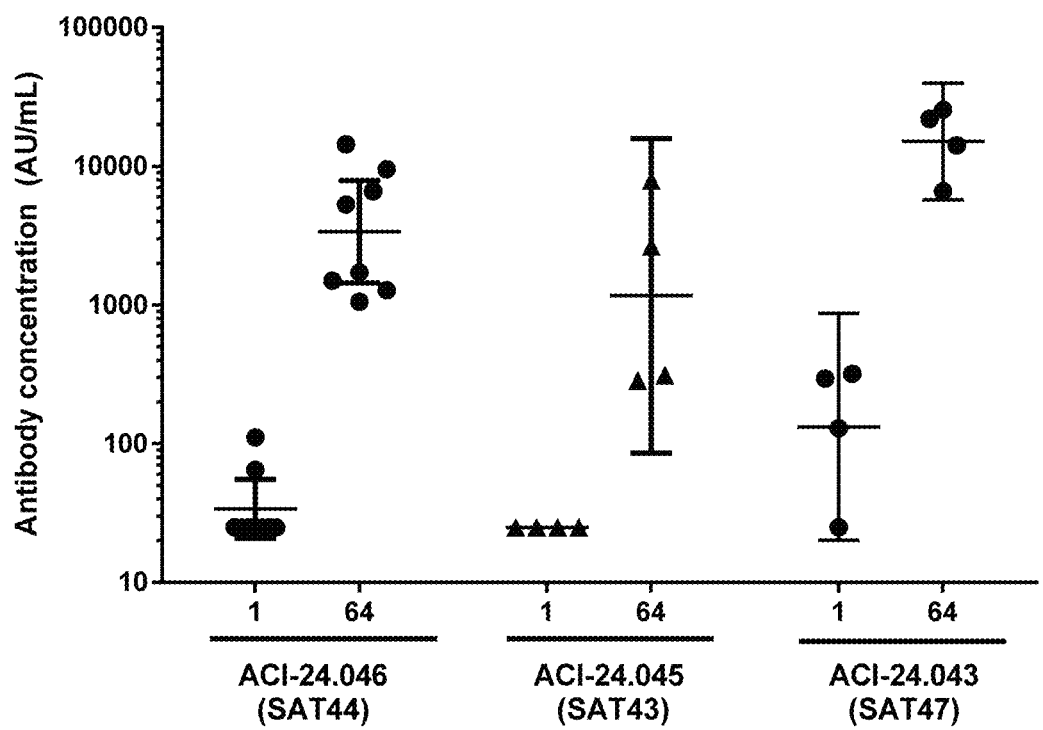
FIG. 5. Analysis of Aβ oligomer-specific IgG antibodies by MSD in serum of Cynomolgus monkeys before the first immunization (Day 1) and 1 week after the third immunization (Day 64) in ACI-24.046 (SAT44, n=8), ACI-24.045 (SAT43, n=4) or ACI-24.043 (SAT47, n=4) immunized monkeys. Results are expressed as geometric mean+/−95% CI of AU/mL. The X axis indicates the individual plasma from groups immunized with indicated vaccines while the Y axis indicates the antibody titers expressed by AU/mL.

The results showed that all tested vaccines ACI-24.046 (encapsulated SAT44), ACI-24.043 (encapsulated SAT47) and ACI-24.045 (encapsulated SAT43) induced an increase of antibodies able to recognize Aβ oligomers at day 64 (1 week after third immunization) compared with day 1 (prior to first immunization); see FIG. 5.

REFERENCES

Adolfsson O., Pihlgren M., Toni N., Varisco Y., Buccarello A. L., Antoniello K., Lohmann S., Piorkowska K., Gafner V., Atwal J. K., Maloney J., Chen M., Gogineni A., Weimer R. M., Mortensen D. L., Friesenhahn M., Ho C., Paul R., Pfeifer A., Muhs A., Watts R. J., *An effector-reduced anti-β-amyloid (Aβ) antibody with unique aβ binding properties promotes neuroprotection and glial engulfment of Aβ*. J Neurosci. July 11; 32(28):9677-89 (2012).

Agadjanyan M. G., Ghochikyan A., Petrushina I, Vasilevko V., Movsesyan N., Mkrtichyan M., Saing T. and Cribbs D. H., *Prototype Alzheimer's Disease Vaccine Using the Immunodominant B Cell Epitope from β-Amyloid and Promiscuous T Cell Epitope Pan HLA DR-Binding Peptide*. J Immunol 174 (3) 1580-1586 (2005).

Arai H, Suzuki H, Yoshiyama T. *Vanutide cridificar and the QS-21 adjuvant in Japanese subjects with mild to moderate Alzheimer's disease: results from two phase 2 studies*. Curr Alzheimer Res. 12(3):242-54 (2015).

Ghochikyan A., Mkrtichyan M., Petrushina I., Movsesyan N., Karapetyan A., Cribbs D. H., Agadjanyan M. G., *Prototype Alzheimer's disease epitope vaccine induced strong Th2-type anti-Abeta antibody response with Alum to Quil A adjuvant switch*. Vaccine. 20; 24(13):2275-82 (2006).

Gilman S., Koller M., Black R. S., Jenkins L., Griffith S. G., Fox N. C., Eisner L., Kirby L., Boada Rovira M., Forette F., Orgogozo J. M., *Clinical effect of Aβ immunization (AN1792) in patients with AD in an interrupted trial*. Neurology 64, 1553-1562 (2005).

Liu B., Frost J. L., Sun J., Fu H., Grimes S., Blackburn P., Lemere C. A., *MER5101, a novel Aβ1-15:DT conjugate vaccine, generates a robust anti-Aβ antibody response and attenuates Aβ pathology and cognitive deficits in APPswe/PS1ΔE9 transgenic mice*. J Neurosci. 33(16): 7027-37 (2013).

Lutzner N., Kalbacher H., *Quantifying Cathepsin S Activity in Antigen Presenting Cells Using a Novel Specific Substrate*. J. Biol. Chem. Vol. 283 No. 52 p. 36185 (2008).

Maier M., Seabrook T. J., Lazo N. D., Jiang L., Das P., Janus C, Lemere C. A., *Short amyloid-beta (Abeta) immunogens reduce cerebral Abeta load and learning deficits in an Alzheimer's disease mouse model in the absence of an Abeta-specific cellular immune response*. J Neurosci. 3; 26(18):4717-28 (2006).

Martineau P, chapter 41: Affinity Measurements by Competition ELISA, Pages 657-665, from book: Antibody engineering, Vol. 1; R. Kontermann and S. Dübel (2010)

Monsonego A., Weiner H. L., *Immunotherapeutic approaches to Alzheimer's disease*. Science. 31; 302 (5646):834-8 (2003).

Muhs A., Hickman D. T., Pihlgren M., Chuard N., Giriens V., Meerschman C., van der Auwera I., van Leuven F., Sugawara M., Weingertner M.-C., Bechinger B., Greferath R., Kolonko N., Nagel-Steger L., Riesner D., Brady R. O., Pfeifer A., Nicolau C., *Liposomal vaccines with conformation-specific amyloid peptide antigens define immune response and efficacy in APP transgenic mice*. PNAS, 104 23:9810-9815 (2007).

Orgogozo J. M., Gilman S., Dartigues J. F., Laurent B., Puel M., Kirby L. C., Jouanny P., Dubois B., Eisner L., Flitman S., Michel B. F., Boada M., Frank A., Hock C., *Subacute meningoencephalitis in a subset of patients with AD after Abet42 immunization*. Neurology 61: 46-54 (2003).

Pihlgren M., Silva A. B., Madani R., Giriens V., Waeckerle-Men Y., Fettelschoss A., Hickman D. T., López-Deber M. P., Ndao D. M., Vukicevic M., Buccarello A. L., Gafner V., Chuard N., Reis P., Piorkowska K., Pfeifer A., Kündig T. M., Muhs A., Johansen P., *TLR4- and TRIF-dependent stimulation of B lymphocytes by peptide liposomes enables T cell-independent isotype switch in mice*. Blood. January 3; 121(1):85-94 (2013).

Sallusto F., Lanzavecchia A., Araki K., Ahmed R., *From vaccines to memory and back*. Immunity. October 29; 33(4):451-63 (2010).

Schneeberger A., Mandler M., Mattner F., Schmidt W., *AFFITOME® technology in neurodegenerative diseases: the doubling advantage*. Hum Vaccin. 11:948-52 (2010)

Seabrook T. J., Thomas K., Jiang L., Bloom J., Spooner E., Maier M., Bitan G., Lemere C. A., *Dendrimeric Abeta1-15 is an effective immunogen in wildtype and APP-tg mice*. Neurobiol Aging. 28(6):813-23 (2006).

Siegrist C A, Chapter 2: Vaccine Immunology, Pages 14-32 from book: Vaccine (6$^{th}$ Edition, 2013).

Soto C., *Plaque busters: strategies to inhibit amyloid formation in Alzheimer's disease*. Molecular Medicine Today (vol 5), August 1999.

Winblad B., Graf A., Riviere M. E., Andreasen N., Ryan J. M., *Active immunotherapy options for Alzheimer's disease*. Alzheimers Res Ther. 2014 Jan. 30; 6(1):7.

Winblad B., Andreasen N., Minthon L., Floesser A., Imbert G., Dumortier T., Maguire R. P., Blennow K., Lundmark J., Staufenbiel M., Orgogozo J. M., Graf A., *Safety, tolerability, and antibody response of active Aβ immunotherapy with CAD106 in patients with Alzheimer's disease: randomised, double-blind, placebo-controlled, first-in-human study*. Lancet Neurol. 11(7):597-604 (2012).

Unless defined otherwise, all technical and scientific terms used herein have the same meanings as commonly understood by one of ordinary skill in the art to which this invention belongs. All publications and patents specifically mentioned herein are incorporated by reference in their entirety for all purposes in connection with the invention.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate.

The invention claimed is:

1. A liposomal vaccine composition comprising:
   a. A β-amyloid (Aβ)-derived peptide antigen displayed on the surface of a liposome;
   b. A peptide comprising a universal T-cell epitope encapsulated within the liposome that stimulates a helper T-cell response that enhances antibody production by B-cells,
      wherein the peptide comprises:
         i. the amino acid sequence of SEQ ID NO: 6 and the tetanus toxin domain of SEQ ID NO: 1;
         ii. the amino acid sequence of SEQ ID NO: 8, the tetanus toxin domain of SEQ ID NO: 2, and an immunogenic keyhole limpet hemocyanin (KLH) domain;
         iii. the amino acid sequence of SEQ ID NO: 8 and the tetanus toxin domain of SEQ ID NO: 3; or
         iv. an immunogenic influenza hemagglutinin domain, the diphtheria toxin domain of SEQ ID NO: 4, the tetanus toxin domain of SEQ ID NO: 4, and the Epstein Barr virus domain of SEQ ID NO: 4; and
   c. An adjuvant.

2. The liposomal vaccine composition of claim 1 wherein the peptide comprising a universal T-cell epitope comprises at least 30% hydrophobic amino acids.

3. The liposomal vaccine composition of claim 1 wherein the liposomal vaccine composition comprises at least two different universal T-cell epitopes encapsulated within the liposome.

4. The liposomal vaccine composition of claim 3 wherein each universal T-cell epitope is no more than 30 amino acids in length.

5. The liposomal vaccine composition of claim 1 wherein the liposomal vaccine composition comprises two, three or four different universal T-cell epitopes encapsulated within the liposome.

6. The liposomal vaccine composition of claim 1 wherein the peptide comprising a universal T-cell epitope comprises at least two different universal T-cell epitopes.

7. The liposomal vaccine composition of claim 1 wherein the peptide comprising a universal T-cell epitope comprises two, three or four universal T-cell epitopes.

8. The liposomal vaccine composition of claim 7 wherein at least two of the two, three or four universal T-cell epitopes are joined by a linker.

9. The liposomal vaccine composition of claim 8 wherein the linker comprises at least two amino acids.

10. The liposomal vaccine composition of claim 1 wherein the peptide comprising a universal T-cell epitope comprises an amino acid sequence selected from SEQ ID NO: 1 (SAT42), SEQ ID NO: 2 (SAT43), SEQ ID NO: 3 (SAT44), and SEQ ID NO: 4 (SAT47).

11. The liposomal vaccine composition of claim 1 wherein the adjuvant forms part of the liposome.

12. The liposomal vaccine composition of claim 1 wherein the adjuvant comprises monophosphoryl lipid A (MPLA), CpG, or both MPLA and CpG.

13. The liposomal vaccine composition of claim 1 wherein the peptide comprising a universal T-cell epitope is between 30 and 60 amino acids in length.

14. The liposomal vaccine composition of claim 6 wherein the peptide comprising a universal T-cell epitope is between 30 and 60 amino acids in length.

15. A kit for treating, preventing, inducing a protective immune response against or alleviating the symptoms associated with an amyloid-beta associated disease or condition in a subject comprising the liposomal vaccine composition of claim 1 together with instructions for administering the vaccine composition.

16. A liposomal vaccine composition comprising:
a. A tetrapalmitolyated β-amyloid (Aβ)-derived peptide antigen displayed on the surface of the liposome that comprises, consists essentially of or consists of amino acids 1-15 of Aβ;
b. A peptide comprising a universal T-cell epitope encapsulated within the liposome wherein the peptide comprising a universal T-cell epitope comprises an amino acid sequence of SEQ ID NO: 3 (SAT44); and
c. An adjuvant.

17. The liposomal vaccine composition of claim 16 wherein the adjuvant forms part of the liposome.

18. The liposomal vaccine composition of claim 16 wherein the adjuvant comprises monophosphoryl lipid A (MPLA), CpG, or both MPLA and CpG.

19. A liposomal vaccine composition comprising:
a. A tetrapalmitolyated β-amyloid (Aβ)-derived peptide antigen displayed on the surface of the liposome that comprises, consists essentially of or consists of amino acids 1-15 of Aβ;
b. A peptide comprising a universal T-cell epitope encapsulated within the liposome wherein the peptide comprising a universal T-cell epitope comprises, consists essentially of or consists of an amino acid sequence of SEQ ID NO: 4 (SAT47); and
c. An adjuvant.

20. The liposomal vaccine composition of claim 19 wherein the adjuvant forms part of the liposome.

21. The liposomal vaccine composition of claim 19 wherein the adjuvant comprises monophosphoryl lipid A (MPLA), CpG, or both MPLA and CpG.

22. The liposomal vaccine composition of claim 9, wherein the linker comprises, consists essentially of, or consists of the amino acids VVR or PMGAP (SEQ ID NO:11).

23. The liposomal vaccine composition of claim 3 wherein each universal T-cell epitope is no more than 20 amino acids in length.

* * * * *